United States Patent
Strobel et al.

(10) Patent No.: US 7,192,939 B2
(45) Date of Patent: Mar. 20, 2007

(54) PESTALOTIOPSIS MICROSPORIA ISOLATES AND COMPOUNDS DERIVED THEREFROM

(75) Inventors: Gary Strobel, Bozeman, MT (US); Eugene Ford, Tok, AK (US); James K. Harper, Spanish Fork, UT (US)

(73) Assignee: Montana State University, Bozeman, MT (US)

( * ) Notice: Subject to any disclaimer, the term of this patent is extended or adjusted under 35 U.S.C. 154(b) by 314 days.

(21) Appl. No.: 10/356,320

(22) Filed: Jan. 30, 2003

(65) Prior Publication Data
US 2004/0009573 A1    Jan. 15, 2004

Related U.S. Application Data

(60) Provisional application No. 60/352,254, filed on Jan. 30, 2002.

(51) Int. Cl.
A01N 57/00 (2006.01)
C07D 305/12 (2006.01)
C07D 307/93 (2006.01)

(52) U.S. Cl. .................. 514/100; 549/307; 549/462

(58) Field of Classification Search .............. 435/126, 435/254.1; 549/462, 307, 429; 514/99
See application file for complete search history.

(56) References Cited

U.S. PATENT DOCUMENTS

| | | | |
|---|---|---|---|
| 4,297,487 A | 10/1981 | Mueller | |
| 4,305,889 A | 12/1981 | Kodaira et al. | |
| 4,322,466 A | 3/1982 | Tomlinson | |
| 4,411,910 A | 10/1983 | Schroeder et al. | |
| 4,415,720 A | 11/1983 | Rose | |
| 4,448,603 A | 5/1984 | Nakayama et al. | |
| 4,484,760 A | 11/1984 | Rach | |
| 4,548,948 A | 10/1985 | Ward et al. | |
| 4,650,884 A | 3/1987 | Bogeso | |
| 4,737,508 A | 4/1988 | Lovey et al. | |
| 4,766,125 A | 8/1988 | van Daele | |
| 4,877,801 A | 10/1989 | Lovey et al. | |
| 4,943,590 A | 7/1990 | Boegesoe et al. | |
| 4,954,544 A | 9/1990 | Chandaria | |
| 5,100,456 A | 3/1992 | Tsantrizos et al. | |
| RE34,712 E | 8/1994 | Boegesoe et al. | |
| 5,411,967 A | 5/1995 | Kao et al. | |
| 5,430,056 A | 7/1995 | Peck et al. | |
| 5,460,647 A | 10/1995 | Snedeker et al. | |
| 5,523,075 A | 6/1996 | Fuerst et al. | |
| 5,523,476 A | 6/1996 | Seki et al. | |
| 5,532,029 A | 7/1996 | Fuerst et al. | |
| 5,648,504 A | 7/1997 | Seki et al. | |
| 5,658,902 A | 8/1997 | Ahn et al. | |
| 5,665,697 A | 9/1997 | Boden et al. | |
| 5,677,107 A | 10/1997 | Neckers | |
| 5,773,444 A | 6/1998 | Ahn et al. | |
| 5,837,645 A | 11/1998 | Fuerst et al. | |
| 5,942,554 A | 8/1999 | Ren et al. | |
| 5,997,891 A | 12/1999 | Fuerst et al. | |
| 6,002,020 A | 12/1999 | Geissler et al. | |
| 6,071,947 A | 6/2000 | D'Alessio et al. | |
| 6,093,838 A | 7/2000 | Vasudevan et al. | |
| 6,180,650 B1 | 1/2001 | Frenette et al. | |
| 6,365,747 B1 | 4/2002 | Dall/Asta et al. | |
| 6,492,374 B2 | 12/2002 | Andersen et al. | |

FOREIGN PATENT DOCUMENTS

| | | |
|---|---|---|
| EP | 0 528 612 A2 | 2/1993 |
| EP | 0528612 | 2/1993 |
| WO | WO 00/56894 A1 | 9/2000 |

OTHER PUBLICATIONS

Pahari et al. Tetrahedron Letters (1998), (2004), 45(26), 5109-5112.*
Strobel, G., et al., "Isopestacin, an isobenzofuranone from *Pestalotiopsis microspore*, possessing antifungal and antioxidant activities," *Phytochemistry* 60(2):179-183 (May 2002).
Morrison and Boyd, Organic Chemistry, Fourth Edition, Allyn and Bacon, NY (1983) pp. 968-969.
Achenbach, et al., "Phthalide und Chromanole.aus *Aspergillus duricaulis*" Liebigs Ann. Chem., 1985, 1596-1628.
Database, NCBI, Accession No. AF346561. Feb. 26, 2001, see entire listing.
Kirmse, et al., "Carbenes and the O—H bonds: Hydroxyalkyl-substituted arylcarbenes", *J. Org. Chem.*, 1990, 55, 2325-2332.
Naito et al., "Two New Phenolic Reductones from *Aspergillus terreus*", Tetrahedron Lett. 1969; 53, 4675-4678.
Schultz, B. 2001 British Mycological Society, International Symposium Proceedings, Bioactive Fungal Metabolites-impact and Exploitation. University of Wales, Apr.) Mycol. Res. 106 (9) : 996-1004 (2002).
Strobel et al. "Isopestacin, and isobenzofuranone from *Pestalotiopsis microspora*, possessing antifungal and antioxidant activities.", *Phytochemistry*, May 2002, vol. 60, No. 2, pp. 179-183.
Stroebel et al., "Taxol from *Pestalotiopsis microspore*, an endophytic fungus of *Taxus wallachiania*" Microbiology, 1996, 142, 435-440.
Wan, et al., "1995 Merck Forsst Award Lecture Quinone methides: relevant intermediates in organic chemistry" Can. J. Chem., 1996, 74, 465-475.

* cited by examiner

Primary Examiner—Sandra E. Saucier
(74) Attorney, Agent, or Firm—Robin M. Silva; Sean D. Solberg; Dorsey & Whitney LLP

(57) ABSTRACT

The present invention relates to the novel isolated 12–30 strain of *Pestalotiopsis microspora* capable of producing novel antioxidant and antimycotic agents. The present invention also relates to the novel isolated 3,5,7 trisubstituted isobenzofuranone and derivatives thereof, methods of isolating the novel isobenzofuranone from cultures *P. microspora* 12–30, and to novel uses of the compound as an antioxidant and antimycotic agent. The present invention further relates to a novel 1,5,7 trisubstituted 1,3-dihydroisobenzofuran and derivatives thereof, methods of isolating this novel compound from cultures of *Pestalotiopsis microspora* 12–30, and to uses thereof.

9 Claims, 5 Drawing Sheets

AF377301. Pestalotiopsis sp...[gi:21310057]

gi|21310057|gb|AF377301.1| Pestalotiopsis sp. NG12-30 internal transcribed spacer 1, 5.8S ribosomal RNA gene and internal transcribed spacer 2, complete sequence; and 28S ribosomal RNA gene, partial sequence TAGAGTTTTCTAAACTCCCAACCCATGTGAACTTACCTTTTGTTGCCTCGGCAGGA
GTTATAGGTCTTCTTATAGCTGCTGCCGGTGGACCATTAAACTCTTGTTATTTTAT
GTAATCTGAGCGTCTTATTTTAATAAGTCAAAACTTTCAACAACGGATCTCTTGG
TTCTGGCATCGATGAAGAACGCAGCGAAATGCGATAAGTAATGTGAATTGCAGA
ATTCAGTGAATCATCGAATCTTTGAACGCACATTGCGCCCATTAGTATTCTAGTG
GGCATGCCTGTTCGAGCGTCATTTCAACCCTTAAGCCTAGCTTAGTGTTGGGAAT
CTACTTCTTTATAGTTGTAGTTCCTGAAATACAACGGCGGATTTGTAGTATCCTCT
GAGCGTAGTAATTTTTTTCTCGCTTTTGTTAGGTGCTATAACTCCCAGCCGCTAAA
CCCCCAATTTTTTGTGGTTGACC

FIG._1

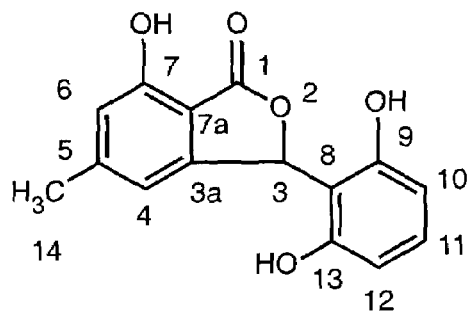

(1) Numbered Structure of Isopestacin

FIG._2

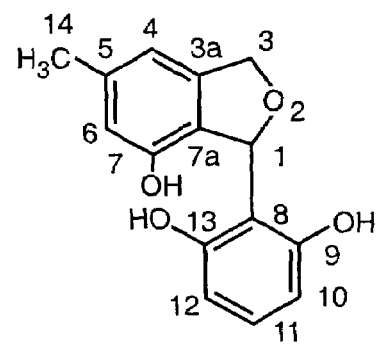

FIG._3

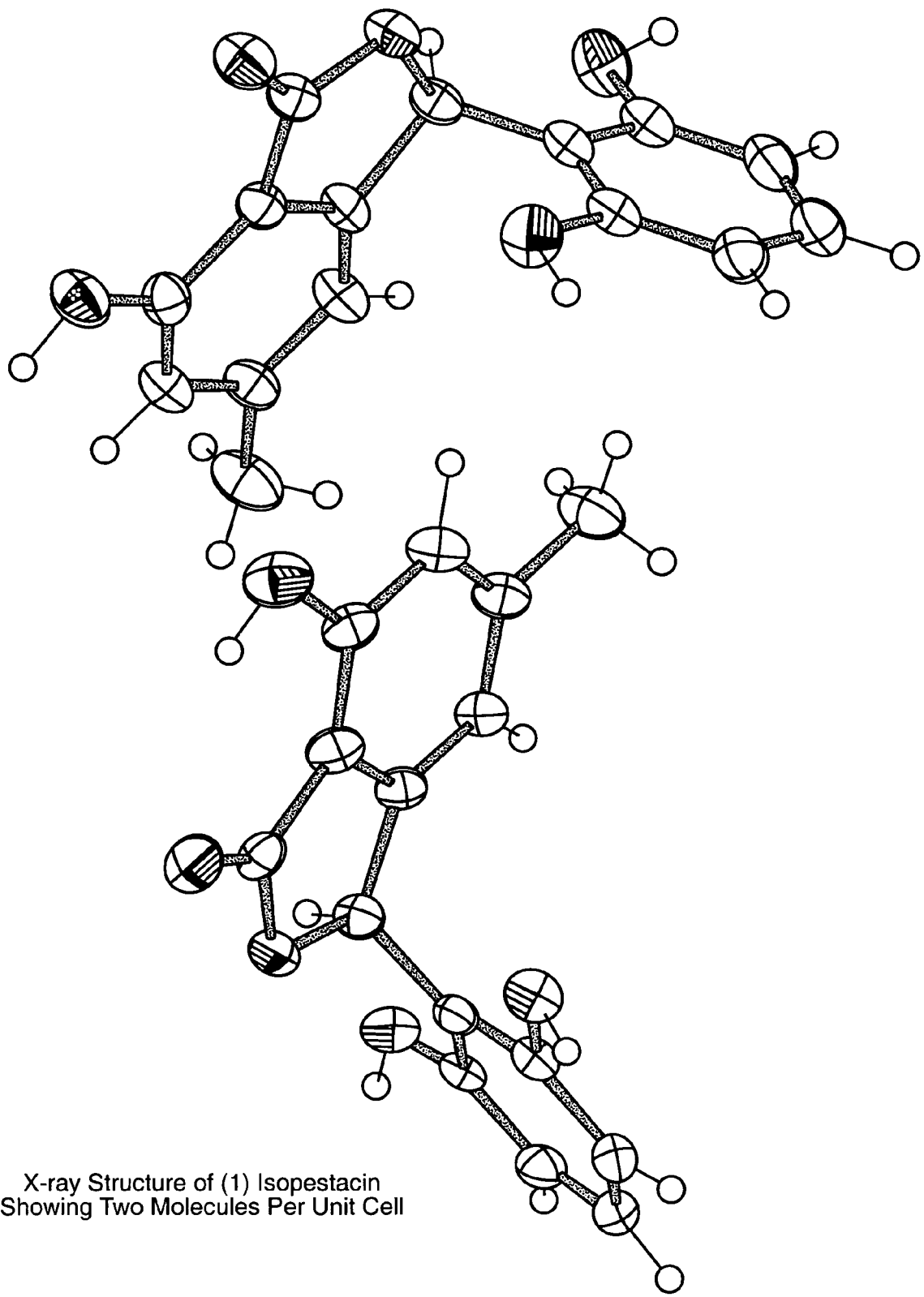
FIG._4

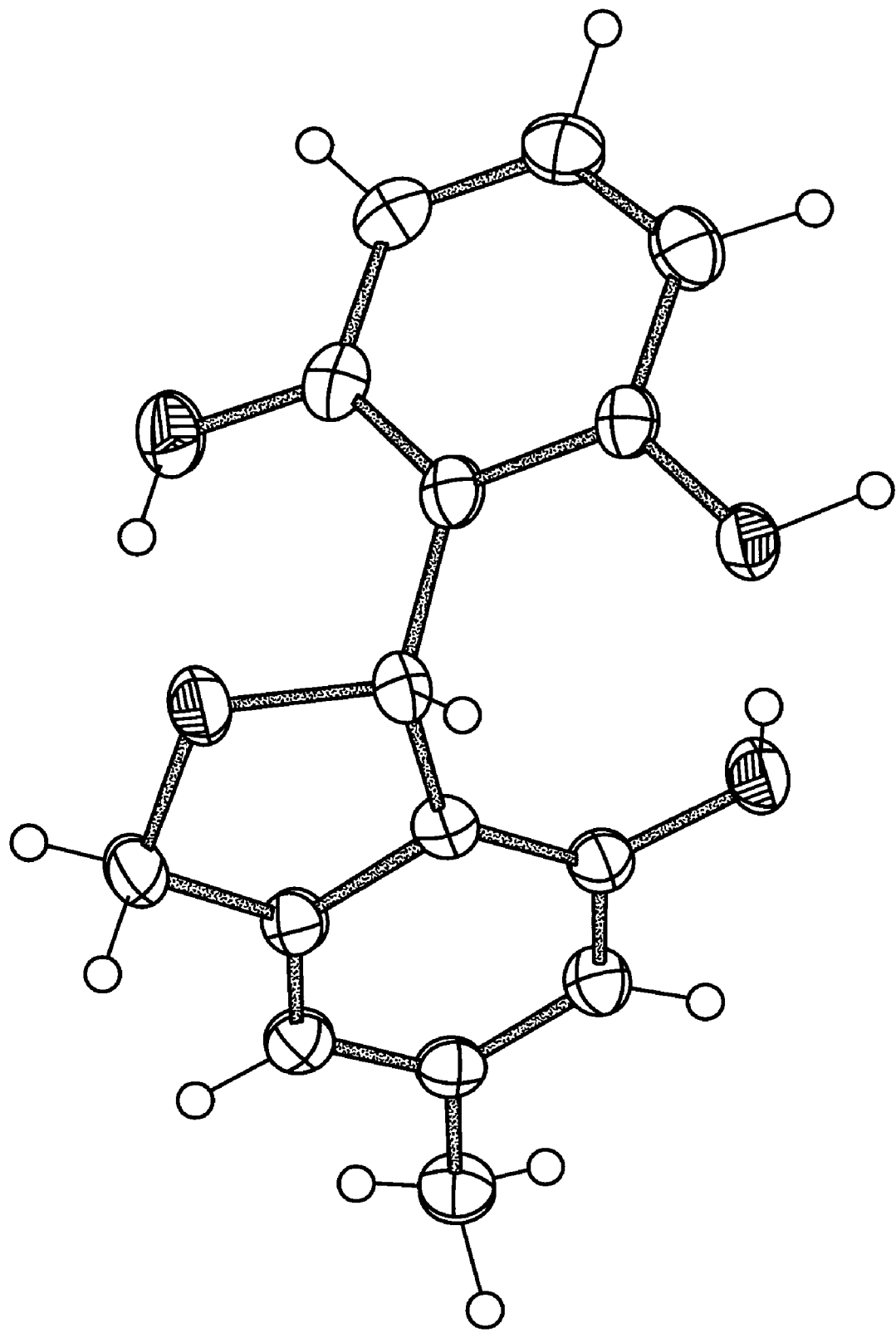
FIG._5

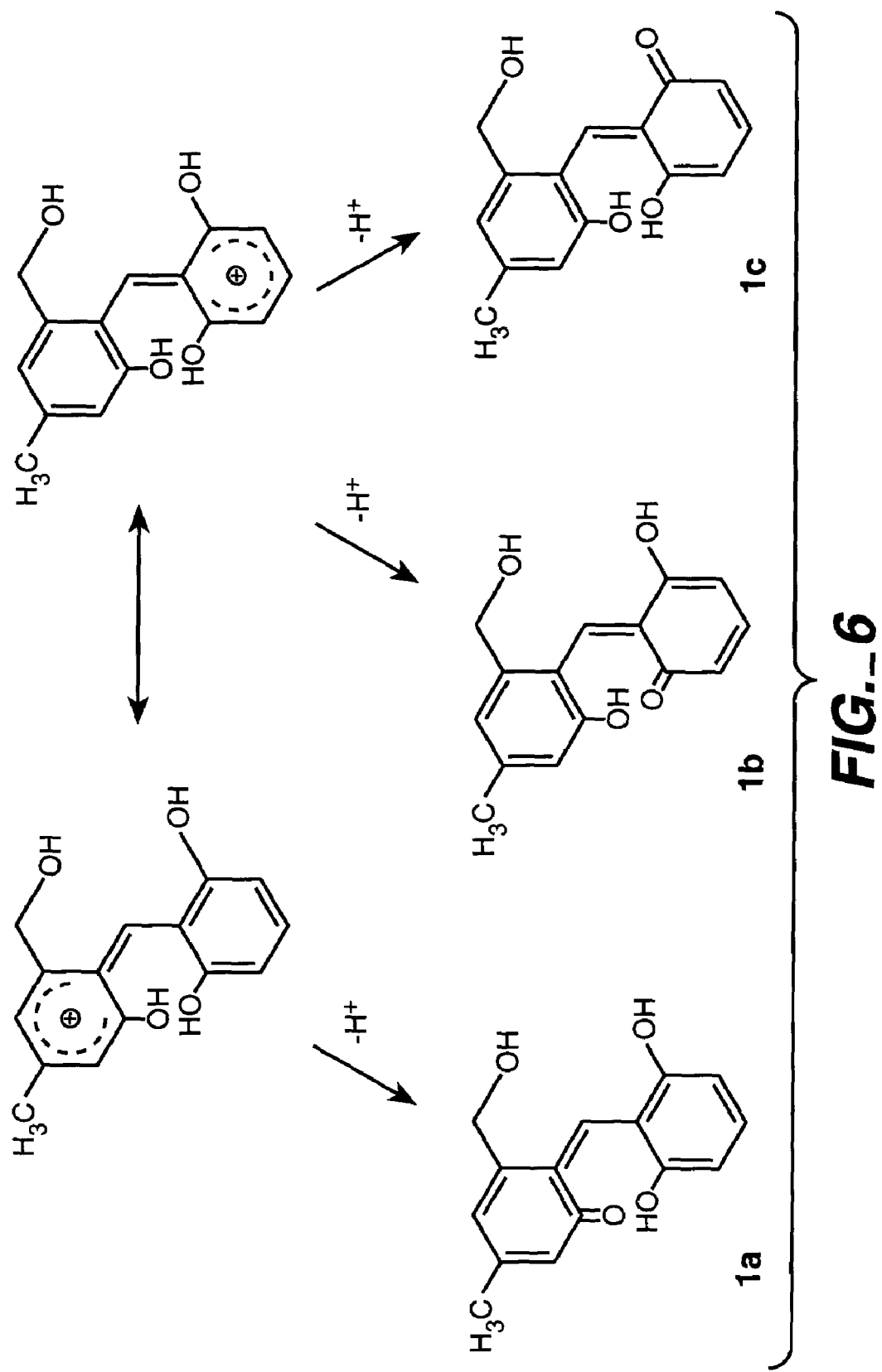
FIG._6

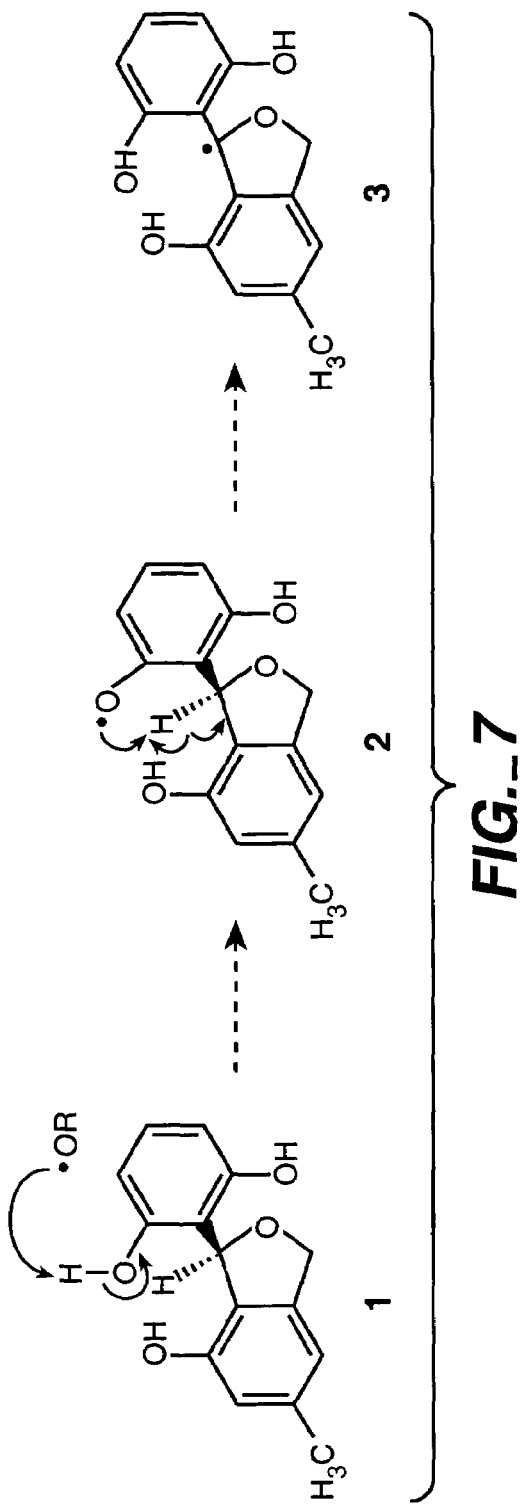
FIG._7
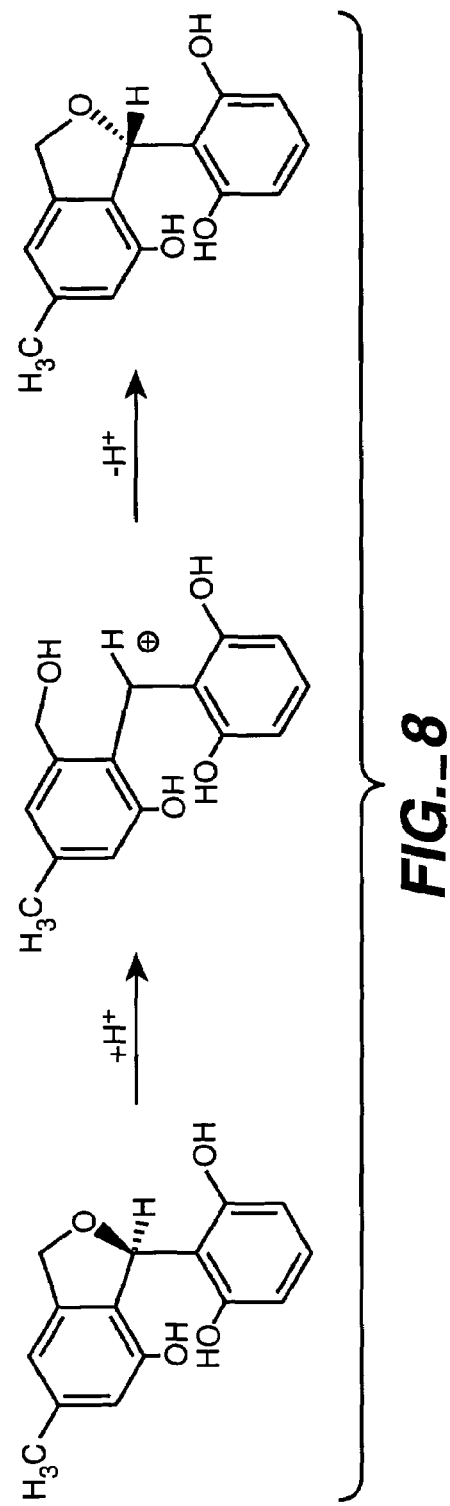
FIG._8

PESTALOTIOPSIS MICROSPORIA ISOLATES AND COMPOUNDS DERIVED THEREFROM

CROSS REFERENCE TO RELATED APPLICATIONS

This application is a continuation-in-part application of U.S. Ser. No. 60/352,254, filed Jan. 30, 2002, incorporated by reference in its entirety.

GOVERNMENTAL SUPPORT OF APPLICATION

This invention was made with governmental support under grant number GM08521-40, awarded by the National Institutes of Health. The United States government has certain rights in the invention.

FIELD OF THE INVENTION

The present invention relates to the novel isolated 12-30 strain of *Pestalotiopsis microspora* capable of producing novel antioxidant and antimycotic agents. The present invention also relates to the novel isolated 3,5,7 trisubstituted isobenzofuranone and derivatives thereof, methods of isolating the novel isobenzofuranone from cultures *P. microspora* 12-30, and to novel uses of the compound as an antioxidant and antimycotic agent. The present invention further relates to a novel 1,5,7 trisubstituted 1,3-dihydroisobenzofuran and derivatives thereof, methods of isolating this novel compound from cultures of *Pestalotiopsis microspora* 12-30, and to uses thereof.

BACKGROUND OF THE INVENTION

It has been estimated that there may be as many as 1 million different fungal species on our planet (Hawksworth, D. C. and A. Y. Rossman, A. Y., 1987. "Where are the undescribed fungi?", *Phytopath.* 87, 888–891). In the past century, many of the 0.1 million fungi that have been described have been those associated with various higher organisms as either parasites or saprophytes on dead and dying biological materials. Thus, the question, where are the remaining 0.9 million fungi? It turns out that microorganisms seem to occupy virtually every living and non-living niche on earth. This includes those in the thermal vents, in deep rock sediments, and in desert as well as marine environments.

In the past few decades, plant scientists have begun to realize that plants may be serving as a reservoir of untold numbers of organisms known as endophytes (Bacon, C. W., and White, J. F. 2000. *Microbial Endophytes*. Marcel Deker Inc., N.Y.). Endophytic fungi and bacteria are those organisms living within the tissues of host plants. By definition, these microorganisms (mostly fungi and bacteria) live in the intercellular spaces of plant tissues. Typically, endophytes coexist with their hosts without any pathogenic symptoms. These organisms have proven to be an unusually rich source of novel bioactive natural products. One of the most ubiquitous endophytic fungi is *Pestalotiopsis microspora*. This microorganism produces a plethora of bioactive organic substances including the anticancer drug taxol. Stroebel, G.; Yang, X.; Sears, J.; Kramer, R.; Sidhu, R. S.; Hess, W. M. *Microbiology* 1996, 142, 435–440. However, because of the enormous genetic diversity of *P. microspora*, each individual isolate is generally unique in the spectrum of substances that it produces.

Some of these endophytes may be producing bioactive substances that, in some way may, be involved in the host-endophyte relationship. As a direct result of the role that these secondary metabolites may play in nature, they may ultimately be shown to have applicability in medicine, agriculture and industry. We are now wittnessing the beginning a worldwide scientific effort to isolate endophytes and study their natural products. While there are myraids of epiphytic microorganisms associated with plants, the endophytic ones seem to be attracting more attention. This may be the case since closer biological associations may have developed between these organisms in their respective hosts than the epiphytes or soil related organisms. Hence, the result of this may be the production of a greater number and diversity of classes of biological derived molecules possessing a range of biological activities. In fact, a recent comprehensive study has indicated that 51% of biologically active substances isolated from endophytic fungi were previously unknown (Schutz, B. 2001. British Mycological Society, International Symposium Proceedings, Bioactive Fungal Metabolites—Impact and Exploitation. University of Wales, April). This compares with only 38% novel substances from soil microflora.

One of the least studied biochemical-chemical systems in nature is the relationship existing between microorganisms and their plant hosts. For instance, it does appear that all higher plants are hosts to one or more endophytic microbes. These microbes include the fungi, bacteria and actinomycetes. They reside in the tissues beneath the epidermal cell layers. It is well understood that endophytic infections are at least inconspicuous (Bacon, C. W., and White, J. F. 2000. Microbial Endophytes. Marcel Deker Inc., N.Y.). And as a result, the host tissues are transiently symptomless and the colonization of the tissues is internal to the surface of the plant. The exact physical relationship of the endophyte to the plant has, in most cases remained obscure, because it is extremely difficult, by electron microscopic techniques, to find an endophyte within plant tissues. Conceivably, the microbes live within the intercellular spaces of the tissues and it also seems likely that penetration of living cells may occur but not easy to observe. The relationship that any given endophyte establishes with the plant varies from symbiotic to that bordering on pathogenic.

It also turns out that these relationships may have begun to evolve from the time that higher plants first appeared on the earth hundreds of millions years ago. Evidence of plant associated microbes has been discovered in the fossilized tissues of stems and leaves (Bacon, C. W., and White, J. F. 2000. Microbial Endophytes. Marcel Deker Inc., N.Y.). As a result of these long held associations, it is possible to imagine that some of these endophytic microbes may have devised genetic systems allowing for the transfer of information between themselves and the higher plant and visa versa. Obviously, this would permit a more rapid and reliable mechanism of the endophyte to deal with ever changing environmental conditions and perhaps allow for more compatibility with the plant host. In addition, independent evolution of the endophytic microbes may have allowed them to better adapt to a plant host and perhaps develop to a point where they could contribute to their relationship to their host plant by carrying out such functions as protection from pathogens, insects, and other grazing animals. Or in still another case, it is possible to imagine that certain products from the endophyte may protect the plant from the harmful effects of irradiation, oxidation, and other events that occur as a natural consequence on living on this earth.

P. microspora fungal strains are some of the most commonly isolated endophytic fungi associated with rainforest plants (Schutz, B. 2001. British Mycological Society, International Symposium Proceedings, Bioactive Fungal Metabolites—Impact and Exploitation. University of Wales, April). These strains differ widely in the degree and diversity of secondary metabolites that they may produce. Bioactive compounds such as taxol, jesterone, ambuic acid, torreyanic acid, pestaloside, pestalotiopsins and 2-α-hydroxydimeniol are but a few examples that illustrate this point (Schutz, B. 2001. British Mycological Society, International Symposium Proceedings, Bioactive Fungal Metabolites—Impact and Exploitation. University of Wales, April).

Compounds with antioxidant capabilities are of interest to industries and companies wishing to sell products having the innate ability to protect human skin and other organs from the effects of numerous free radicals that form as free radical oxygen and hydroxyls react with structural and functional features of living organisms and render them inactive or unable to properly function. Fungal isolates of *P. microspora* possessing both antioxidant and antifungal properties are rare or non-existent.

Thus, it is an object of the present invention to provide cultures of an isolate of *P. microspora*, termed *P. microspora* 12-30, and compounds isolated therefrom that exhibit both antioxidant and antimycotic activity.

BRIEF SUMMARY OF THE INVENTION

Accordingly, the present invention provides methods for producing a number of compounds that possess both antioxidant and antimycotic activity. These compounds, designated isopestacin and pestacin, and their derivatives, are able to scavenge free radical oxygen and free radical hydroxyl ion and render them inactive in their destructive action against biological moieties such as proteins and lipids that are vital to normal metabolic functions, such as the destructive action in skin.

Another aspect of the present invention, therefore, provides pharmaceutically acceptable compositions which comprise a therapeutically-effective amount of pestacin, isopestacin or derivatives thereof, such as described above, formulated together with one or more pharmaceutically acceptable carriers (additives) and/or diluents for use as an antioxidant as a prophylactic or therapeutic agent for the treatment of free radical induced tissue damage or as an antimycotic agent in the treatment of fungal infections. The pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intravectally, for example, as a pessary, cream or foam. The compounds and pharmaceutic compositions provided by the present invention are especially useful for the topical treatment of wounds to promote tissue healing. Their antimycotic activity may be useful prophylactically or therapeutically to treat fungal systemic or surface infections of animal or human patients.

The compounds and derivatives thereof of the present invention are also useful for the treatment of fungal infections or colonizations of plant tissues. The compounds may be applied to the target plant by, for example, injection dipping, spraying or any other means that is appropriate for contacting the target fungus with the active antimycotic agent.

BRIEF DESCRIPTION OF THE DRAWINGS

FIG. 1 depicts the nucleic acid sequence SEQ ID NO:1.
FIG. 2 depicts the structure of isopestacin.
FIG. 3 depicts the structure of pestacin.
FIG. 4 depicts the asymmetric unit of crystallized isopestacin.
FIG. 5 depicts the asymmetric unit of crystallized pestacin.
FIG. 6 depicts the proposed racemization mechanism of pestacin
FIG. 7 depicts the antioxidant mechanism of pestacin
FIG. 8 depicts the resonance stabilized intermediated intermediates.

DETAILED DESCRIPTION OF THE INVENTION

The present invention is directed to biologically pure cultures of an isolate of *Pestalotiopsis microspora*, herein designated *P. microspora* 12-30, that produces several compounds of interest, including compounds possessing both antioxidant and antimycotic activity. These compounds, designated isopestacin and pestacin, and their derivatives, are able to scavenge free radical oxygen and free radical hydroxyl ion and render them inactive in their destructive action against biological moieties such as proteins and lipids that are vital to normal metabolic functions, such as the destructive action in skin. The compounds, therefore, are useful as therapeutic agents for the prevention or treatment of tissue damage induced by free radicals. The novel compounds of the present invention also have antimycotic activity and are, therefore, useful in inhibiting the proliferation of fungi, especially phytopathogens such as, for example, *Pythium ultimum*.

Accordingly, the present invention provides biologically pure cultures of the *P. microspore* isolate designated 12-30. By "biologically pure" or grammatical equivalents herein is understood in the art to mean a culture fluid or plate that contains a single type of organism. In general, as applied to the current invention, tissue fragments from *Terminalia morobensis* are placed in either culture fluid or agar (e.g. mycological agar) until fungal growth occurs. Fungal hyphae from the fungal growth is grown and serially transferred until a culture in pure form is obtained, as measured by observation (e.g. morphological and/or genetic unity).

The *P. microspore* 12-30 isolate can be identified and characterized in a variety of ways, most notably that cultures of *P. microspore* 12-30 exhibit both antimycotic activity (particularly against *Pythium ultimum*) and antioxidant activity, as further defined below. Fungal cultures possessing both bioactivities is rarely if ever seen in *P. microspora*, regardless of the origin of the culture. In addition, *P. microspora* 12-30 has been deposited in the Montana State University living culture collection and designated as such. Further, certain genetic sequences of the organism have been elucidated, namely its ITS, 5.8S and ITS2 sequences depicted in FIG. 1 (SEQ ID NO:1) and are deposited in GenBank under accession number AF 377301.

In addition, *P. microspora* 12-30 is obtained as an endophyte from a stem of *Terminalia morobensis*. It was identified on the basis of its 5-celled conidium possessing characteristic appendages (Worapong, J., 2001. Taxonomy, Molecular Phylogeny and Taxol Production in Selected Genera of Endophytic Fungi. PhD. Dissertation, Montana State University, Bozeman, Mont.). Its ITS1, 5.8S, and ITS2 sequences have been deposited in GenBank as AF 377301 and the relationship of this fungus to other *Pestalotia* spp. and *Pestalotiopsis* spp. on the basis of genetic and structural characteristics have been described by (Worapong, J., 2001. Taxonomy, Molecular Phylogeny and Taxol Production in Selected Genera of Endophytic Fungi. PhD. Dissertation, Montana State University, Bozeman, Mont.). The host plant of this fungus was collected on the shores of the Karawari River in the Sepik drainage on the north coast of Papua New Guinea at 4° 23' 39"South and 143° 18' 49"East. *P. microspora*, isolate 12-30, was only one of many endophytes recovered from this tree. It was acquired from a section of a small tree stem (0.75 cm in diameter) using previously described techniques (Stroebel, G.; Yang, X.; Sears, J.; Kramer, R.; Sidhu, R. S.; Hess, W. M. *Microbiology* 1996, 142, 435–440) as further described below.

The biologically pure culture can be in a variety of forms, including, but not limited to, still cultures (particularly MID media), stored stocks of mycelium and/or hyphae (particularly glycerol stocks) and freeze dried stocks, particularly of spores and/or mycelium.

The present invention provides the isobenzofuranone isopestacin and its derivatives. While only a few other isobenzofuranones are known from natural sources, isopestacin is the only one having a substituted benzene ring attached at the C3 position of the furanone ring. Isopestacin (1-oxo-3-(9,13-dihydroxybenzene)-5-methyl-7-hydroxy-1, 3-dihydrobenzofuranone) has the formula shown in Structure (1):

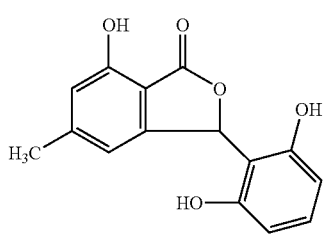

Structure 1

In a preferred embodiment, isopestacin derivatives are provided. A number of suitable derivatives are shown below, although as will be appreciated by those in the art, other derivatives can be included as well.

Depicted in the figures are a variety of substitutent groups labeled "R". Suitable R substitutent groups include, but are not limited to, hydrogen, halogens, alkyl (and all its derivatives outlined below), aryl (and all its derivatives outlined below), alcohol (including ethylene glycols), alkoxy, amino, amido, nitro, ethers, esters, aldehydes, sulfonyl, silicon moieties, halogens, sulfur containing moieties, phosphorus containing moieties. In the structures depicted herein, R is hydrogen when valence so requires and the position is otherwise unsubstituted. It should be noted that some positions may allow two substitution groups, R and R', in which case the R and R' groups may be either the same or different. In general, preferred structures that require both R and R' have one of these groups as a hydrogen. In addition, R groups on adjacent carbons, or adjacent R groups, can be attached to form cycloalkyl or cycloaryl groups, including heterocycloalkyl and heterocycloaryl groups (and substituted derivatives thereof) together with the carbon atoms of the ring. These may be multi-ring structures as well.

By "alkyl group" or grammatical equivalents herein is meant a straight or branched chain alkyl group, with straight chain alkyl groups being preferred. If branched, it may be branched at one or more positions, and unless specified, at any position. The alkyl group may range from about 1 to about 30 carbon atoms (C1–C30), with a preferred embodiment utilizing from about 1 to about 20 carbon atoms (C1–C20), with about C1 through about C12 to about C15 being preferred, and C1 to C5 or C6 being particularly preferred, although in some embodiments the alkyl group may be much larger. Also included within the definition of an alkyl group are cycloalkyl groups such as C5 and C6 rings, and heterocyclic rings with nitrogen, oxygen, sulfur or phosphorus. Alkyl also includes heteroalkyl, with heteroatoms of sulfur, oxygen, nitrogen, and silicon being preferred. Typical heteroatoms and/or heteroatomic groups which can replace the carbon atoms include, but are not limited to, —O—, —S—, —S—O—, —NR'—, —PH—, —S(O)—, —S(O)$_2$—, —S(O)NR'—, —S(O)$_2$NR'—, and the like, including combinations thereof, where each R' is independently selected. Alkyl includes substituted alkyl groups. By "substituted alkyl group" herein is meant an alkyl group further comprising one or more substitution moieties "R", as defined above. Alkyl includes alkenyl and alkynyl as well. "Alkenyl" by itself or as part of another substituent refers to an unsaturated branched, straight-chain or cyclic alkyl having at least one carbon—carbon double bond derived by the removal of one hydrogen atom from a single carbon atom of a parent alkene. The group may be in either the cis or trans conformation about the double bond(s). "Alkynyl" by itself or as part of another substituent refers to an unsaturated branched, straight chain or cyclic alkyl having at least one carbon—carbon triple bond derived by the removal of one hydrogen atom from a single carbon atom of a parent alkyne. Aralkyl refers to an alkyl group substituted with an aryl group, defined below.

"Aryl" by itself or as part of another substituent refers to a monovalent aromatic hydrocarbon group having the stated number of carbon atoms (i.e., C5–C15 means from 5 to 15 carbon atoms) derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronen, fluoranthene, fluorene, hexacene, hexaphene, hexalene, as-indacene s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like, as well as the various hydro isomers thereof. In preferred embodiments, the aryl group is (C5–C15) aryl, with (C5–C10 being even more preferred. Particularly preferred aryls are phenyl and substituted phenyl.

By "alkoxyl" herein is meant —OR, with R being a group as defined herein. Particularly preferred are —OC1-C3, with methyoxy and ethoxyl being particularly preferred.

By "amino groups" or grammatical equivalents herein is meant —NH$_2$, —NHR and —NR$_2$ groups, with R being as defined herein.

By "nitro group" herein is meant an —NO$_2$ group.

By "sulfur containing moieties" herein is meant compounds containing sulfur atoms, including but not limited to, thia-, thio- and sulfo-compounds, thiols (—SH and —SR), and sulfides (—RSR—). By "phosphorus containing moieties herein is meant compounds containing phosphorus, including, but not limited to, phosphines and phosphates. By "silicon containing moieties" herein is meant compounds containing silicon.

By "ether" herein is meant an —O—R group. Preferred ethers include alkoxy groups, with —O—(CH2)2CH3 and —O—(CH2)4CH3 being preferred.

By "ester" herein is meant a —COOR group.

By "halogen" herein is meant bromine, iodine, chlorine, or fluorine. Preferred substituted alkyls are partially or fully halogenated alkyls such as CF3, etc.

By "aldehyde" herein is meant —RCOH groups.

By "alcohol" herein is meant —OH groups, and alkyl alcohols —ROH.

By "amido" herein is meant —RCONH— or RCONR— groups.

Preferred derivatives of isopestacin are shown below:

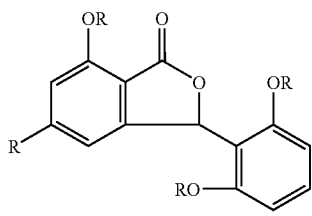

Structure 2

In Structure 2, R is a substitution group as outlined herein, except disfavored bonds as are appreciated by those in the art are avoided, as for all the structures outlined herein. Preferred embodiments for all the structures depicting an —OR alkoxy group include R as lower alkyl (C1–C3), with methoxy being especially preferred. In Structure 2, one or two of the —OR groups may also be —OH. The R group in the 5 position is preferably a lower alkyl as well, with C1–C3 being preferred and methyl and ethyl being particularly preferred.

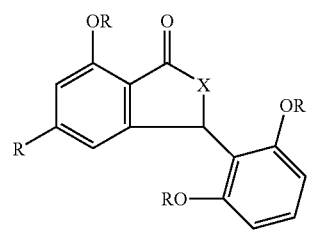

Structure 3

In this structure and others depicting an X moiety, the X is a heteroatom, generally selected from oxygen, nitrogen and sulfur. In the case of nitrogen, secondary amines are preferred (e.g. X comprises —NH), although in some instances a tertiary amine (e.g. X comprises —NR) can be used, with R being defined herein

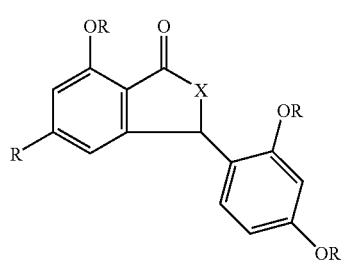

Structure 4

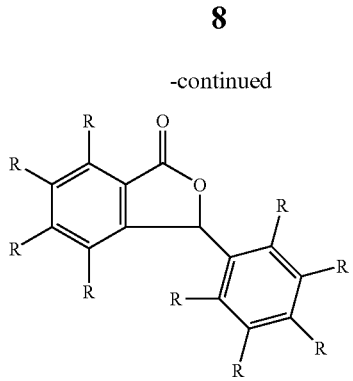

Structure 5

In this embodiment, the R groups are independently selected from the list of substituents outlined herein. In general, preferred embodiments in these Structures utilize one or two independent substituent R groups on each benzyl ring; that is, either a single or two non-hydrogen R groups are preferred. Preferred embodiments for the benzyl at the 5 position include the case where: a) two R groups comprise hydroxy with the remainder substituents being hydrogen; b) one R group is hydroxy and one is alkoxy with the remainder substituents being hydrogen; c) two alkoxy groups with the remainder substituents being hydrogen.

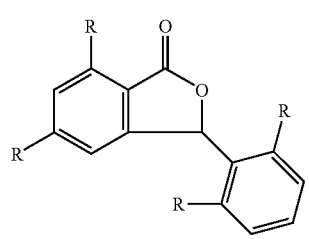

Structure 6

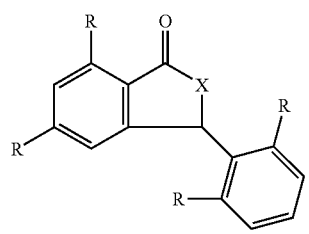

Structure 7

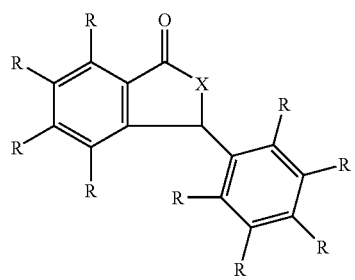

Structure 8

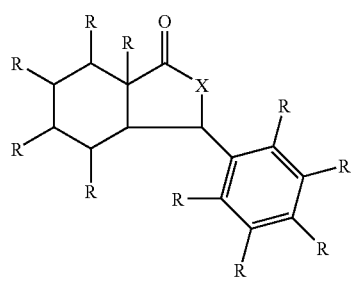

Structure 9

In this embodiment, a cycloalkyl ring, rather than a benzyl ring, can be used. Furthermore, although the Structure depicted in Structure 9 depicts an optionally substituted benzyl ring at the 3 position of the furanone (assuming X is O), it is also possible that the cycloalkyl and benzyle groups are switched; e.g. the 3 position group is a cycloalkyl and the other ring is a benzyl group (e.g. a benzofuranone substituted at the 3 position with a cycloalkyl).

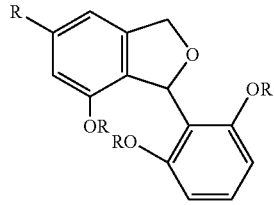

Structure 13

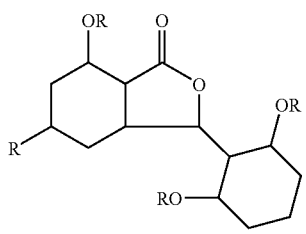

Structure 10

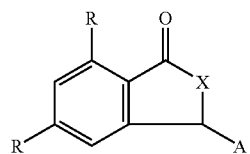

Structure 11

In Structure 11, A can be an aryl group (included substituted aryl, heteroaryl or substituted heteroaryl, and multi-ring structures, including aryl—aryl, biaryl groups as well as aryl-alkyl ring structures).

In addition to the isopestacin derivatives of the invention, the invention provides 1,5,7 trisubstituted 1,3-dihydroisobenzofuran pestacin and pestacin derivatives. Pestacin exhibits antioxidant activity 11 times greater than the vitamin E derivative troxol and displays antifungal activities as well. It occurs naturally as a racemic mixture. Only three other naturally occurring 1,3-dihydroisobenzofurans have been previously observed and pestacin represents the first 1,5,7 trisubstituted natural product. The structure of pestacin is shown below:

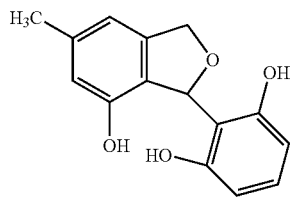

Structure 12

In a preferred embodiment, pestacin derivatives are provided. A number of suitable derivatives are shown in below, although as will be appreciated by those in the art, other derivatives can be included as well.

Preferred derivatives of pestacin are shown below. It should be need that while most of the structures are based on furans, the oxygen atom can be replaced with nitrogen and sulfur.

As noted above for isopestacin, preferred embodiments include R as lower alkyl and —OR as lower alkoxy.

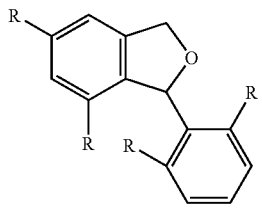

Structure 14

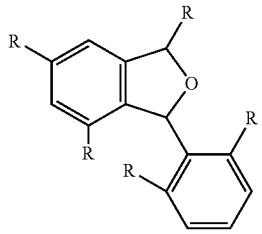

Structure 15

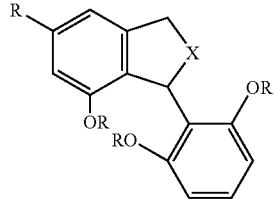

Structure 16

In this structure and others depicting an X moiety, the X is a heteroatom, generally selected from oxygen, nitrogen and sulfur. In the case of nitrogen, secondary amines are preferred (e.g. X comprises —NH), although in some instances a tertiary amine (e.g. X comprises —NR) can be used, with R being defined herein.

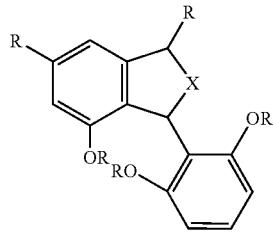

Structure 17

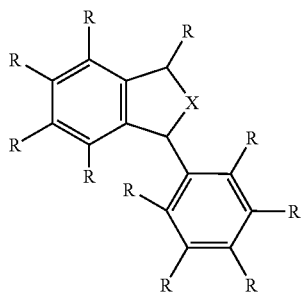

Structure 18

In this embodiment, the R groups are independently selected from the list of substituents outlined herein. In general, preferred embodiments in these Structures utilize one or two independent substituent R groups on each benzyl ring; that is, either a single or two non-hydrogen R groups are preferred. Preferred embodiments for the benzyl at the 3 position include the case where: a) two R groups comprise hydroxy with the remainder substituents being hydrogen; b) one R group is hydroxy and one is alkoxy with the remainder substituents being hydrogen; c) two alkoxy groups with the remainder substituents being hydrogen.

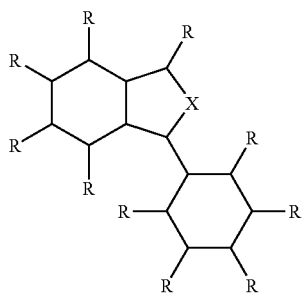

Structure 19

In this embodiment, a cycloalkyl ring, rather than a benzyl ring, can be used at either or both positions, with the structure depicted above utilizing both.

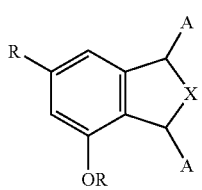

Structure 20

In Structure 20, A can be an aryl group (included substituted aryl, heteroaryl or substituted heteroaryl, and multi-ring structures, including aryl-aryl, biaryl groups as well as aryl-alkyl ring structures). As noted below, 1-aryl-1,3-dihydro isobenzofurans are known to undergo electrophilic substitution when treated with alkali metals under proper conditions. Azzena, U.; Demartis, S.; Melloni, G. *J. Org. Chem.* 1996, 61, 4913–4919. Accordingly, preferred embodiments of Structure 20 include R as lower alkyl (with methyl particularly preferred), —OR as hydroxy, the 1 position A being a lower aryl or substituted lower aryl, and the 3 position A being a substituted aryl, particular the 9, 13 dihydroxy benzyl derivative.

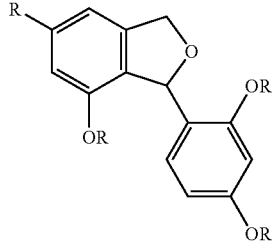

Structure 21

It should be noted that in the case of pestacin derivatives, two independent non-hydrogen substitutents off the 3 position are generally disfavored.

Structure 22

In Structure 22, all R groups can be as defined herein, Preferred embodiments include wherein $R_1$ and $R_2$ are individually selected from hydrogen and 1,3 dihydrophenyl, $R_1$ and $R_2$ together form a carbonyl group and $R_3$ is hydrogen or 1,3 dihydrophenyl, wherein any one of $R_1$, $R_2$ and $R_3$ is dihydroxyphenyl, and wherein $R_4$ is selected from any of —R', —C(=O)R', —C(=O)NR'R" and —C=NR'C(=O)OR', and wherein R', R" and $R_5$ are individually selected from the group consisting of hydrogen, a lower straight-chain alkyl, a lower branched alkyl, and an aromatic group selected from the group consisting of pyridinyl, quinolinyl, pyrimidinyl, phenyl and benzyl, or a substituted derivative thereof. In Structure 22, it should be noted that the other positions can be substituted with other R groups, and the noted hydrogens can also be R groups, although as outlined herein, preferably a single carbon does not have two non-hydrogen substitutents.

The compounds of the present invention are synthesized in a variety of ways. In a preferred embodiment, cultures of *P. microspora* 12-30 are grown and the compositions purified as outlined in the examples. In addition, as is known in the art, general purification schemes for small molecules are well known in the art, and include a variety of crystallographic and chromatographic techniques (thin layer, silica, reverse phase, liquid systems including but not limited to HPLC).

Yet another aspect of the present invention is a method for isolating an isobenzofuran, comprising the steps of obtaining a biologically pure culture of a fungus capable of producing an isobenzofuranthe, wherein the isobenzofuran may be the iosbenzonfuranone 1-oxo-3-(9,13-dihydroxy-benzene)-5-methyl-7-hydroxy-1,3 dihydrobenzofuranone (Isopestacin) (3) or 1-(9,13-dihydroxybenzene-7-hydroxy-5-methyl-1,3-dihydrobenzenefuran (Pestacin) (2), culturing the fungus in a medium, whereby the fungus produces the isobenzofuran in the medium, and isolating the isobenzofuran from a culture medium.

In one embodiment of this aspect of the present invention, the method further comprises extracting the medium with a first organic solvent, evaporating the first organic solvent to form a solid residue, dissolving the solid residue in a second organic solvent to form a solution, contacting the solution from step (e) with silica gel, thereby binding the isobenzofuran to the silica gel; washing the silica gel with at least one wash fluid, and washing the silica gel with an elutant, thereby eluting the isobenzofuran from the silica gel in an eluant.

One embodiment of the present invention further comprises the step of crystallizing the isobenzofuran from the eluant.

In one embodiment of the present invention the first organic solvent is methylene chloride and the isobenzofuran may be 1-(9,13-dihydroxybenzene-7-hydroxy-5-methyl-1,3-dihydrobenzenefuran (Pestacin) (2).

In another embodiment of the present invention, the second organic solvent is chloroform, the at least one wash fluid is chloroform, the elutant is chloroform-ethyl acetate in a ratio of about 10:1 v/v and the steps (e)–(h) are repeated to give a substantially pure preparation of the isobenzofuran in the eluant.

In this embodiment of the present invention the isobenzofuran may be the iosbenzonfuranone 1-oxo-3-,(9,13-dihydroxybenzene)-5-methyl-7-hydroxy-1,3 dihydrobenzofuranone (Isopestacin) (3).

In another embodiment of the present invention, the elutant is chloroform, steps (e)–(h) are repeated and the elutant is chloroform-acetonitrile (100:1 v/v).

Alternatively, when pestacin and isopestacin derivatives are utilize, these derivatives can be synthesized in a variety of ways as will be appreciated by those in the art. In general, there are general techniques outlined in the following references that can be followed to synthesize 1,3 dihydro isobenzofuran derivatives and 1,5,7 trisubstituted isobenzofuranones (Hans Achenbach et al., Liebigs Ann. Chem., 1985, 1596–1628; Naito, S.; Kaneko, Y. Tetrahedron Lett. 1969; 53, 4675–4678 U.S. Pat. Nos. 6,093,838; 4,943,590; 4,305,889; 4,297,487, 6,002,020; 6,492,374; 6,365,747; 6,071,947; 5,658,902; 4,877,801; 5,773,444; 4,548,948; 4,737,508; 4,650,884; 5,411,967; RE 34,712; 4,411,910; 4,766,125; 4,484,760; 5,532,029; 6,180,650; 4,448,603; 4,415,720; 5,460,647; 5,648,504; 5,677,107; 4,954,544; 5,665,697; 5,100,456; 5,837,645; 5,523,075; 5,942,554; 5,997,891; 5,430,056; 5,523,476; 4,322,466; all of which are incorporated herein by reference). In addition, preparation of pestacin derivatives is be straightforward given the well-documented reactivity of o-quinone methides with nucleophiles. Wan, P.; Barker, B.; Diao, L.; Fischer, M.; Shi, Y.; Yang, C. Can. J. Chem. 1996, 74, 465–475.

While the compounds described herein can be prepared biosynthetically, they need not be prepared biosynthetically. Those of skill in the art can prepare the compounds and derivatives thereof using well known techniques, and compounds produced synthetically are also intended to be within the scope of the present invention. Further, the compounds can be derivatized using well known chemistry, using the naturally-produced materials as starting materials (i.e., a mixture of biosynthesis and chemical synthesis), or by purely chemical synthesis. Representative examples of derivatization chemistry are described in more detail below.

Friedel-Crafts Chemistry. The aromatic ring in the isobenzofuran structure includes a methyl group and a phenol group. As such, the ring can easily be modified by electrophilic aromatic substitution, for example, Friedel-Crafts alkylation and acylation chemistry. These reactions are well known and generally involve reacting the aromatic ring with one or two equivalents of a suitable alkyl halide olefin, or acid halide in the presence of a Lewis acid such as aluminum chloride. Commercially, olefins can be preferred as they are less costly than alkyl halides. In one embodiment, isobutylene is used to provide a t-butyl group ortho and/or para to the phenol group. The presence of bulky t-butyl groups is known to improve antioxidant properties by stabilizing the phenoxy radical, as seen, for example, in compounds such as BHT (butylated hydroxy toluene). In those embodiments where the compounds include a 1,3-dihydroxybenzyl moiety, this moiety can also be derivatized using similar chemistry.

Phenol Derivatization. The phenol group(s), including those on the isobenzofuran ring and/or the 1,3-dihydroxybenzyl moieties can be derivatized with labile groups to form prodrugs. Upon administration, the in vivo removal of the labile groups can release the parent antioxidant compounds in a time release manner. Ester groups are one example of a labile group, and among these ester groups, fatty acid esters can be preferred. The parent compounds can also be conjugated to phospholipids, and the modified phospholipids can be incorporated into emulsions or liposomes. Additional prodrug forms include carbonates and carbamates. Carbamates can be synthesized, for example, by reaction with an appropriate isocyanate. Other prodrug forms of hydroxy/phenoxy groups are well known in the art and are intended to be within the scope of the present invention.

One or more of the phenol groups can also optionally be converted to ethers, for example, using either Mitsunobu or Williamson conditions. However, to retain the antioxidant property, the compounds should retain at least one phenol moiety.

(c) Further Options for Modifying the Aromatic Rings. In addition to or in place of the Friedel-Crafts acylation and/or alkylation chemistry described above, the aromatic rings (in the benzoisofuran and/or 1,3-dihydroxybenzyl moieties) can be modified using additional known reactions, if desired. For example, nitration, sulfonation, halogenation, nitrosation, carbonation, and aldehyde formation (for example, via a Reimer-Tiemann reaction using chloroform and sodium hydroxide) of phenols, which typically occurs at the ortho and para positions, are all well known reactions (see, for example, Morrison and Boyd, Organic Chemistry, Fourth Edition, Allyn and Bacon, NY, (1983), pages 968–969). Such derivatization would be expected to modify the antioxidant and antimycotic properties of the compounds.

The phenol group(s) can be used as templates for library formation by reacting them with a variety of acylating agents (e.g., acid chlorides and anhydrides) and isocyanates to produce derivatives with ester and carbamate substituents in any or all of the phenol moieties. The aromatic rings can be used as templates for providing a variety of substituted aromatic rings for use in preparing a compound library. The libraries can be screened for optimal antioxidant and/or antimycotic properties for example, using high throughput screening methods. Libraries of prodrugs can also be prepared and optionally screened for suitable bioavailability and/or biological activity.

Those compounds described herein that include one or more chiral carbons (i.e., those compounds with two different groups at a single (non-aromatic) ring carbon) can be present in racemic form, or in enantiomerically enriched form. As discussed above, even when prepared using the fungi described herein, the compounds may exist as a racemic mixture, presumably formed post-biosynthetically. Such racemic mixtures can be purified using conventional techniques, representative examples of which are described in more detail below.

The derivatives can be produced as single enantiomers, for example, by using the single enantiomers of the isobenzofuran starting materials. For example, the 1,3-dihydroxybenzyl moieties, if present, are covalently linked to chiral carbons, which can be present as racemic mixtures or purified enantiomers. Individual enantiomers can be produced, for example, by forming diastereomeric esters (i.e., using a chiral carboxylic acid such as brucine), and resolving the resulting diastereomeric esters. The compounds can be resolved, for example, using enzymatic degradation conditions, reverse phase chromatography, crystallization, and the like. The separated esters can then be hydrolyzed, for example, by treatment with dilute acid or enzymatically, for example, using lipase enzymes, preferably under conditions that do not hydrolyze the lactone moiety present in the isobenzofuranones (where present), to form the desired compounds in enantiomerically purified form.

The compositions of the invention may be secondary metabolites or prodrugs. The term "secondary metabolite" as used herein refers to a biosynthetic product produced by a fungus which is not absolutely required for fungal growth or viability, i.e., for protein synthesis, transcription, DNA replication, or the like (Sebek, 1983; Turner, 1975). Examples of compounds which have been designated is secondary metabolites include antibiotics such as penicillin, ergot alkaloids, cyclosporin, and gibberellins (Wainwright, 1992). For the present invention, "secondary metabolites" include trisubstituted isobenzofurans and derivatives thereof produced by the fungus Pestalotiopsis microspora, strain 12-30 as defined herein.

The term "prodrug" is intended to encompass compounds which, under physiological conditions, are converted into the antioxidant and antifungal agents of the present invention. A common method for making a prodrug is to select moieties which are hydrolyzed under physiological conditions to provide the desired biologically active drug. In other embodiments, the prodrug is converted by an enzymatic activity of the recipient animal or the target fungi.

The compositions of the invention also may comprise racemic mixtures. Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivitization with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts can be formed with an appropriate optically-active acid or base, followed by resolution of the diastereomer thus formed by fractional crystallization or chromatographic means well known in the art, and subsequent purification.

Isopestacin, pestacin and their respective derivatives exhibit several biological activities, including, but not limited to, antifungal activity and antioxidant activity. By "antimycotic" or "antifungal" or grammatical equivalents thereof herein is meant the ability of a compound to retard, decrease or eliminate the growth (e.g. generally inhibit the proliferation) of one or more fungi. This includes fungicidal agents that kills the target fungus or as a fungistatic agent that inhibits the growth of target fungus without immediately killing the cells. Preferred embodiments comprise compounds with antifungal properties against plant pathogenic fungi, although other targets are included as well. The terms "fungus" and "fungi" as used herein refer to, but is not limited to fungi of the genera: *Achlya, Altemaria, Balansia, Bipolaris, Blumeria, Botrytis, Cercospora, Cochliobolus, Curvularia, Cylindrocladium, Drechslera, Entyloma, Erysiphe, Fusarium, Gaeumannomyces, Gerlachia, Gibberella, Guignardia, Leptosphaeria, Magnaporthe, Mucor, Mycosphaerella, Myrothecium, Nigrospora, Peronospora, Phoma, Pseudoperonospora, Pseudocercosporella, Phytophthora, Puccinia, Pyrenophora, Pyricularia, Pythium, Rhizoctonia, Rhizopus, Rhynchosporium, Sarocladium, Sclerophthora, Sclerotium, Septoria, Tilletia, Uncinula, Ustilago, Ustilaginoidea*, and *Venturia*. The terms "fungus" and "fungi" also may refer to fungi of the *Pestalotiopsis* genus, most particularly to *P. microspora*. A particularly preferred antifungal activity is exhibited against oomycete species such as *Pythium* species, particularly *Pythium ultimum*.

Antioxidant activity" refers to the ability of a compound of the present invention to reduce any free radical, most preferably the superoxide and/or the hydroxyl free radicatis that may be generated by reactions within a living cell, organism or plant. That is, antioxidant activity means the ability of the compound to retard, decrease or eliminate oxidative effects, in particular to decrease free radical initiation.

Accordingly, once made, the compositions of the invention find used in a variety of applications.

As a preliminary matter, the biologically pure fungal cultures of *P. microspora* 12-30 find use as production organism for pestacin and/or isopestacin. This may involve doing classical or recombinant mutagenesis on the naturally occurring organism to develop high producing strains. In addition, mutagenesis may be done to alter synthesis to produce derivatives as outlined herein.

Original isolation is done as follows. Tissue fragments from the host plant material is obtained, and placed on agar medium or in liquid culture until fungal growth occurs. Fungal hyphae from the fungal growth are placed on either mycological agar or in liquid culture until a culture in pure form is obtained, as is known in the art.

In addition, the chemical compositions of the invention find use in a variety of applications relating to antioxidant activity. In a preferred embodiment, isopestacin, pestacin and their derivatives may be used in salves and other medicants that might be applied to skin, or other bodily orifices to protect them from degradation, aging and other effects that relate directly to loss of function due to harmful free radicals. Similarly, these compounds may be used as food additives and/or nutraceuticals.

Another aspect of the present invention provides pharmaceutically acceptable compositions which comprise a therapeutically-effective amount of pestacin, isopestacin or derivatives thereof, such as described above, formulated together with one or more pharmaceutically acceptable carriers (additives) and/or diluents for use as an antioxidant as a prophylactic or therapeutic agent for the treatment of free radical induced tissue damage or as an antimycotic agent in the treatment of fungal infections. As described in detail below, the pharmaceutical compositions of the present invention may be specially formulated for administration in sold or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam.

The phrase "therapeutically-effective amount" as used herein means that amount of a compound, material, or composition comprising a pestacin, isopestacin or derivatives thereof according to the present invention which is effective for producing some desired therapeutic effect by scavenging free radicals or acting as an antimycotic.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject antioxidant or antimycotic agent from one organ, or portion of the body, to another organ, or portion of the body. Each carrier must "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Certain embodiments of the present pestacin, isopestacin or derivatives thereof may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of pestacin, isopestacin or derivatives thereof. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", J. Pharm. Sci. 66:1–19).

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of a pestacin, isopestacin or derivatives thereof. These salts can likewise be prepared in situ during the final isolation and purification of the pestacin, isopestacin or derivatives thereof, or by separately reacting derivatives comprising carboxylic or sulfonic groups with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants that may be combined with the pestacin, isopestacin or derivatives thereof of the present invention include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

It is contemplated that formulations of the present invention may include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the pestacin, isopestacin or derivatives thereof which produces a therapeutic effect. Generally, out of one hundred percent, this amount will range from about 0.1 percent to about 99.5 percent of active ingredient, preferably from about 5 percent to about 70 percent, most preferably from about 10 percent to about 30 percent.

Methods of preparing these formulations or compositions include the step of bringing into association a compound of the present invention with the carriers and, optionally, one or more accessory ingredients. In general, the formulations are prepared by uniformly and intimately bringing into association an antioxidant or antimycotic agent of the present invention with liquid carriers, or finely divided solid carriers, or both, and then, if necessary, shaping the product.

Formulations of the invention suitable for oral administration may by in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A pestacin, isopestacin or derivatives thereof of the present invention may also be administered as a bolus, electuary or paste.

In solid dosage forms of the invention for oral administration (capsules, tablets, pills, dragees, powders, granules and the like), the active ingredient is fixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agent, such as agar—agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbent, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like. A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch) glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

The tablets, and other solid dosage forms of the pharmaceutical compositions of the present invention, such as dragees, capsules, pills and granules, may optionally be scored or prepared with coatings and shells, such as enteric coating and other coatings well known in the pharmaceutical-formulating art. They may a so be formulated so as to provide slow or controlled release of the active ingredient therein using, for example, hydroxypropylmethyl cellulose in varying proportion to provide the desired release profile, other polymer matrices, liposomes and/or microspheres. They may be sterilized by, for example, filtration through a bacteria-retaining filter, or by incorporating sterilizing agents in the form of sterile solid composition which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micron-capsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active pestacin, isopestacin or derivatives thereof, may contain suspending agents as, for example, ethoxylated isostearyl alcohols, polyoxyethylene sorbitol and sorbitan esters, microcrystalline cellulose, aluminum metahydroxide, bentonite, agar—agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a pestacin, isopestacin or derivatives thereof of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active pestacin, isopestacin or derivatives thereof, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the pestacin, isopestacin or derivatives thereof in the proper medium. Absorption enhancers can also be used to increase the flux of the drug across the skin. The rate of such flux can be controlled by either providing a rate controlling membrane or dispersing the an antioxidant or antimycotic agent in a polymer matrix or gel.

Ophthalmic formulations, eye ointments, powders, solutions and the like, are also contemplated as being within the scope of this invention.

Pharmaceutical compositions of this invention suitable for parenteral administration comprise one or more of pestacin, isopestacin or derivatives thereof of the invention in combination with one or more pharmaceutically-acceptable sterile isotonic aqueous or nonaqueous solutions, dispersions, suspensions or emulsions, or sterile powders which may be reconstituted into sterile injectable solutions dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and other antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsulated matrices of the subject peptides or peptidomimetics in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

Actual dosage levels of the active ingredients in the pharmaceutical compositions of this invention may be varied so as to obtain an amount of the active ingredient which is effective to achieve the desired therapeutic response, e.g., antioxidant or antimycotic activity, for a particular patient, composition, and mode of administration, without being toxic to the patient.

The selected dosage level will depend upon a variety of factors including the activity of the pestacin, isopestacin or derivatives thereof employed, the route of administration, the time of administration, the rate of excretion of the particular compound being employed, the duration of the treatment, other drugs, compounds and/or materials used in combination with the particular inhibitor employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

It is further contemplated that the pestacin, isopestacin or derivatives thereof of the present invention are useful for the treatment of fungal infections of plants. Effective amounts of the compounds and compositions of the present invention may be topically applied to the surface of the plant, or injected in to the tissue of the plant, either into the vascular bundles or into the supporting tissues thereof. When applied to the surface of the plant the compositions may be sprayed, or applied as a wash, or as a dip wherein the plant is not anchored in the ground but is immersed in a volume of an effective amount of pestacin, isopestacin or derivatives thereof.

Alternatively, a solution of a composition according to the present invention may be applied to the soil surrounding a plant, whereupon the composition may enter the soil and be absorbed by the plant rots to treat a fungal infection or colonization of the roots. The composition may also enter the plant roots and be translocated to another region of the plant by the vascular system, thereby treating a fungal infection or colonization not in the plant roots.

Topical administering of the compounds of the present invention to the surface of a plant may be used to treat surface growth of the fungal phytopathogen, including the reproductive bodies thereof, and may be useful to allow adsorption of the effective antimycotic agents so as to inhibit the proliferation of hyphae invading the tissues of the infected plants.

Besides being useful for the treatment of phytopathogens, as exemplified by the inhibitkon of the oomycete *Pythium ultimum*, treatment of the plant with the pestacin, isopestacin or derivatives thereof of the present invention is useful for the treatment of endophytes, symbiants etc which may not be desirable on, for example, plants destined for importation into a non-native or native habitat. Further, the pestacin, isopestacin or derivatives thereof may be used to selectively inhibit the proliferation of a target species of fungus on a plant, while not affecting, or less so, the proliferation of another, more desirable, species.

EXAMPLES

Example 1

Isolation of *P. Microspora* 12-30 and Isopestacin

The compound was isolated from culture broths of the fungus *P. microspora* 12- 30 and crystallized. Its structure was determined by x-ray crystallography. Both proton and carbon NMR assignments (HMQC and INADEQUATE) are also reported for isopestacin. This compound possesses antifungal activity and, as measured by electron spin resonance specroscopy, it also behaves as an antioxidant scavenging both superoxide and hydroxy free radicals. Thus, isopestacin can be used as an antioxidant, for example for use in creams or salves to protect human skin from the effects of exposure to free radicals that are naturally generated and can have adverse effects on biological systems. Thus, isopestacin, a novel compound, can protect living systems from the detrimental effects of free radicals by scavenging them. Biochemical assays combined with electron spin resonance methods have been used to unequivocally show that isopestacin is an antioxidant.

Isolation of *P. Microspora* 12-30

The host plant of this endophytic fungus, a combretaceaous plant belonging to the genus—*Terminalia*, was collected on the shores of the Karawari River in the Sepik drainage on the north coast of Papua New Guinea at 4° 23' 39"South and 143° 18' 49"East. *P. microspora*, isolate 12-30, was only one of many endophytes recovered from this tree. It was acquired from a section of a small tree stem (0.75 cm in dia) using previously described techniques (Strobel et al., 1996). This fungal culture was purified by removing hyphal tips and plating them on potato dextrose agar. This particular isolate of *P. microspora* was of interest because its antifungal properties as well as the multitude of secondary products that it was making. The culture was designated as 12-30 and stored as hyphae and mycelia in 15% glycerol at −70° C.

Isolation of Isopestacin

*P. microspora* was grown for 35 days at 23° C. under still culture conditions on the M1D medium (Strobel et al., 1996). The mycelium of the fungus was separated from the culture fluid by passing the culture through 4 layers of cheesecloth. The filtrate was extracted with 2 equal volumes of methylene chloride and ultimately taken to dryness by flash evaporation. Approximately 90 mg of residue remained with no more than 50 mg of the residue soluble in chloroform. This $CHCl_3$ solution was placed on a silica gel column (1×8 cm). The column was rinsed with 25 ml of chloroform, followed by 25 ml of a mixture of chloroform: ethyl acetate; 10:1 v/v, and then 25 ml of chloroform: ethyl acetate; 5:1 v/v. Fractions of 5 ml were collected and those containing compound (1), as checked by thin layer chromatography were saved, pooled and rechromatographed on a second silica column (1×8 cm). Pure compound (1) appeared in those fractions eluting with chloroform: ethyl acetate at 10:1 v/v. The fractions were pooled, dried and redissoled in a minimum volume of chloroform and allowed to slowly evaporate at 23° C. until crystals appeared. Purity of the compound was determined by thin layer chromatography in multiple systems.

Thin Layer Chromatography

Thin layer chromatography of fungal fermentation products was performed on Merck silica gel plates (0.25 mm thick) using various solvent systems. Each system is indicated along with the respective $R_F$ value of (1) in it as follows: chloroform: methanol 10:1 v/v ($R_F$=0.28); chloroform: acetonitrile 6:3 V/v ($R_F$=0.28); chloroform: ethyl acetate 9:1 v/v ($R_F$0.03); isopropanol: ethyl acetate: 9:1 v/v ($R_F$=0.83); methylene chloride: n-butanol 5:1 v/v ($R_F$=0.81); ethyl acetate: tetrahydrofuran 3:1 v/v ($R_F$=0.83) and chloroform: methanol: acetic acid 10:1:0.1 v/v/v ($R_F$=0.40). Compound (1) could be detected by its absorption under a short wave UV lamp and its production of a bright red product after spraying with vanillin in sulfuric acid reagent followed by gentle heating (Cardellina, 1991).

X-Ray Crystallographic Methods

A colorless plate shaped crystal 0.32×0.23×0.15 mm in size was mounted on a glass fiber with traces of viscous oil and then transferred to a Nonius Kappa CCD diffractometer equipped with Mo Kα radiation (λ=0.71073 Å). Ten frames of data were collected at 200±1 K with an oscillation range of 1 deg/frame and an exposure time of 20 sec/frame (Nonius, 1998). Indexing and unit cell refinement based on all observed reflection from those ten frames, indicated a monoclinic P lattice. A total of 9451 reflections ($\lambda_{max}$=27.5°) were indexed, integrated and corrected or Lorentz polarization and absorption effects using DENZO-SMN and SCALEPAC (Otwinowski and Minor, 1997). Post refinement of the unit cell gave a=11.8852(2) Å, b=8.1240(3) Å, c=26.9689(8) Å, β=101.8214(19), and V=2548.76(13) $Å^3$. Axial photographs and systematic absences were consistent with the compound having crystallized in the monoclinic space group P $2_1$/c.

A combination of direct methods and heavy atom methods were employed using SIR 97 (Altomare et al., 1997). All of the non-hydrogen atoms were refined with anisotropic displacement coefficients. Hydrogen atoms were located and refined isotropically using SHELXL97 (Sheldrick, 1997). The weighting scheme employed was $w=1/[\sigma^2(F_o^2)+(0.0399P)^2+0.6937P]$ where $P=(F_o^2+2F_c^2)/3$. The refinement converged to R1=0.0462, wR2=0.0934, and S=1.018 for 3866 reflections with 1>2σ(l), and R1=0.0825, wR2=0.1071, and S=1.018 for 5716 unique reflections and 459 parameters. In this case, $R1=\Sigma(||Fo|-|Fc||)/\Sigma|Fo|$, $wR2=[\Sigma(w(Fo^2-Fc^2)^2)/\ \Sigma(Fo^2)^2]^{1/2}$, and S=Goodness-of-fit on $F^2=[\Sigma(w(Fo^2-Fc^2)^2/(n-p)]^{1/2}$, where n is the number of reflections and p is the number of parameters refined. The maximum Δ/σ in the final cycle of the least-squares was <0.001, and the residual peaks on the final difference-Fourier map ranged from −0.204 to 0.229 e/$Å^3$. Scattering factors were taken from the International Tables for Crystallography, Volume C (Maslen et al., 1992; Creagh et al., 1992). Structural figures were prepared using ORTEP3 for windows (Farrugia, 1997). A complete list of refined coordinates together with other revelant data are deposited at the Cambridge Crystallographic Centre.

NMR Analyses

A 2D INADEQUATE was performed on 57 mg of (1) dissolved in 0.2 ml of $CD_3OD$ and placed in a Shigimi tube designed to center the sample within the coil with glass plugs susceptibility matched to the solvent extending beyond the coil. Analysis was performed on a Varian INOVA 500 MHz spectrometer operating at 125.76 MHz. Spectral widths of 20.8 kHz were used in both dimensions with digital resolutions of 40.6 and 0.2 Hz/point acquired in the evolution and acquisition dimensions, respectively. Other parameters included a $^{13}C$ 90° pulse width of 13.3 μs, a temperature of 26° C., a $^1J_{CC}$ value of 70 Hz, and 128 evolution increments of 512 scans each collected. The spectrum was referenced to the central line of $CD_3OD$ at 49.15 ppm. All $^{13}C$ assignments were established using a computer program designed to enhance signal detection (Dunkel et al., 1990; Dunkel et al., 1992

The HMQC analysis was performed on 8 mg of (1) dissolved in $CD_3OD$ using the Shigimi tube described above. Analysis was performed on a Varian INOVA 500 MHz spectrometer using a Varian indirect detection probe. An operating frequency of 500.62 MHz was used and 1024 increments of 8 scans each were collected. Other parameters included spectral widths of 3.3 and 25.4 kHz for the $^1H$ and $^{13}C$ dimensions, respectively, $^1H$ 90° pulse width of 4.7 μs, $^{13}C$ 90° pulse width of 11.0 μs, a $J_{CH}$ value of 140 Hz, a temperature of 26° C., and a total recycle time 3.6 s. Digital resolutions of 0.8 and 24.8 Hz/point were acquired for the $^1H$ and $^{13}C$ dimensions, respectively. Both $^{13}C$ and $^1H$ referencing were done relative to the center line of the $CD_3OD$ multiplets at 49.15 and 3.31 ppm in the respective spectra. The spectrum was acquired without $^{13}C$ decoupling and all signals were evaluated visually.

Electron Spin Resonance Measurements

EPR techniques used in this work are primarily those reported by Sheu et al., 2000 and Zhu and Fung, 2000. All EPR spectra were recorded on a Bruker model ESP 300E spectrometer, X-band operating at a microwave frequency 9.787 gHz, a microwave power of 10 mW, a modulation frequency of 100.0 kHz, and a modulation amplitude of 0.367 mT. The magnetic field range was 334±80 mT, a time constant of 40.96 ms, a receiver gain of $2 \times 10^4$ and a magnetic fieldsweep rate of 0.48 mT/s. The magnetic field spacings are similar to those reported by Zhang et al (2000). The superoxide $O_2^{-\cdot}$ was generated by the action of hypoxanthine or xanthine on water and oxygen through the catalysis of xanthine oxidase. The hydroxyl free radical $OH^{\cdot}$ is generated by the well-known Fenton reaction: $Fe^{2+} + H_2O_2 = Fe^{3+} + OH^- + OH^{\cdot}$, where 0.09 mM ferrous sulfate and 0.18 mM $H_2O_2$ were used. All enzymes and their respective substrates were purchased from Sigma Chemical Co., while other reagents were acquired from Calbiochem, and Life-Tech. The reaction mixture was transferred to an EPR flat tube for signal detection. Also placed in the tube was a spin trap compound-2-ethoxycarbonyl-2-methyl-3,4-dihydro-2H-pyrrole-1-oxide (EMPO) to trap the superoxide. On the other hand, 2-diethoxyphosphoryl-2-methyl-3, 4-dihydro-2H-pyrrole-1-oxide (DEPMPO) (Zhang et al., 2000) was used trap the hydroxyl free radical (Zhang et al., 2000). Test compounds were added to the tube and their effects on signal reduction (antioxidant activity) were monitored. Because of the water insolubility of (1) it was necessary to dissolve it first into a small amount of methanol and then add it to the reaction mixture. Signal intensity was plotted as a function of antioxidant concentration to get an estimate of the amount of compound needed to reduce the superoxide or the free radical hydroxide concentration by 50%.

Antimycotic Activity

The minimum inhibitory concentration of (1) required to give a 100% reduction of growth of a test fungus over a course of two days was determined by dissolving (1) in 1 ml of potato dextrose broth (PDB). An agar plug, 1 cm in dia, containing the test fungus was then added to the broth and the organisms incubated at 23° C. for 48 hr. At that time the plate containing the fungi was examined visually for growth and the concentration of compound reducing growth by 100% was recorded. Fungi tested were each plant pathogenic and included an oomycete—*Pythium ultimum*, an ascomycete—*Sclerotinia sclerotiorum*, and a basidiomycete—*Rhizoctonia solani*.

Isopestacin (1)

Isopestacin was crystallized by slow evaporation from a chloroform solution at room temperature. M.P. (uncorrected) 218–220° C. UV λ max (methanol) (log ε): 214, 247, 287, 298 (3,570, 3,634, 3,592, 3,545, respectively).

TABLE 1

Isopestacin NMR shift assignments.

| Position | δ$^{13}C^a$ | δ$^1H^b$ |
|---|---|---|
| 1 | 173.84 | — |
| 3 | 77.24 | 6.92 (s) |
| 3a | 154.87 | — |
| 4 | 114.54 | 6.52 (s) |
| 5 | 149.00 | — |
| 6 | 116.53 | 6.64 (s) |
| 7 | 157.33 | — |
| 7a | 111.71 | — |
| 8 | 110.32 | — |
| 9 | 158.95$^a$ | — |
| 10 | 107.96$^b$ | 6.29$^c$ (d, J = 8.2 Hz) |
| 11 | 131.53 | 6.96 (t, J = 8.2 Hz) |
| 12 | 107.96$^a$ | 6.27$^c$ (d, J = 8.2 Hz) |
| 13 | 158.95$^b$ | — |
| 14 | 22.14 | 2.3 (s) |

$^{a,b}$These isotropically degenerate peaks were demonstrated to contain two carbons by integration of a 1D $^{13}C$ spectrum collected with $^1H$ decoupling present only during the free induction decay and a 20 s recycle time.

Results

The isolate of *P. microspora* used in this study was obtained as an endophyte from a stem of *Terminalia morobensis*. It was identified on the basis of its 5-celled conidium possessing characteristic appendages (Worapong 2001). Its ITS1, 5.8S, and ITS2 sequences have been deposited in GenBank as AF 377301 and the relationship of this fungus to other *Pestalotia* spp. and *Pestalotiopsis* ssp. on the basis of genetic and structural characteristics have been described by Worapong (2001).

The fungus was grown on the M1D medium and then the culture fit lid extracted with 2 equal volumes of methylene chloride (Strobel et al., 1996). Biological activity against *Pythium ultimum* was used to guide purification of a product that was crystallized after purification by silica gel column chromatography. The product was shown to be homogeneous by thin layer chromatography in a number solvent systems. The yield of this product was about 20 mg per liter of culture medium. After structural elucidation by x-ray crystallography, the compound was shown to be an isobenzofuranone and was termed—isopestacin (1).

Compound (1) appears as slightly yellowish crystalline plates. HRMS(EI) of (1) revealed a MW for this compound at 270.051292. The best fit calculated mass for this molecular species is 270.052824 which accounts for $C_{15}H_{10}O_5$.

The structure of isopestacin was solved by x-ray crystallographic techniques. Isopestacin crystallized with two molecules in the asymmetric unit (2). Carbon and $^1H$ NMR shift assignments were also established using the HMQC and INADEQUATE experiments, respectively (Table 1) and are consistent with the x-ray structural determination of (1).

A total of fourteen 3,5,7-substituted isobenzofuranones have been previously isolated as natural products from such sources as fungi, liverworts and higher plants (Arone et al., 1989; Arone et al., 1990; Asakawa et al., 1986; Dekker et al., 1997 and Kraut et al., 1994). The substituents at positions 5 and 7 are always ether —OH, —CH$_3$, or —OCH$_3$ functionalities. Likewise, there are a variety of different substituents at position C3, however the direct attachment of a substituted benzene rig at this location has no precedent. Therefore, isopestacin (1), although not representing a novel class of natural products, the isobenzofuranones, the 3-benzo-substituent represents a novel structural feature.

Structural similarities of isopestacin to the flavanoids suggests that (1) may possess antioxidant activity. Testing confirms that Isopestacin (1) indeed has antioxidant activity as determined by ESR measurements described in the experimental section. The compound is able to scavenge superoxide O$_2^{-\bullet}$ and OH$^\bullet$ radicals in solution. The superoxide was generated in our experimental set-up by the action of hypoxanthine on water and oxygen via the catalysis of xanthine oxidase. On the other hand OH$^\bullet$ was generated via the Fenton reaction of hydrogen peroxide on ferrous iron. Simultaneously, EPR spectra are recorded of the free electrons associated with the free radicals. Since (1) has a very low solubility in water we dissolved it in a small amount of methanol in prior to its placement in the reaction mixture. We used the spin trapper EMPO to trap O$_2^{-\bullet}$ and ultimately studied the effect of Vitamin C (ascorbic acid), a well known scavenger of free radicals along with (1) under similar conditions. Thus, in order to reduce the free radical O$_2^{-\bullet}$ in the sample by 50% a concentration of 0.013 mM of Vitamin C was needed. In a comparable experiment, at least 0.185 mM of (1) was required to produce a 50% reduction of the ESR signal. Thus, ascorbic acid is at least 14.2 times as effective as (1) as an antioxidant for scavenging the superoxide radical. It should be noted that since superoxide was generated via the xanthine oxidase reaction it was no possible to accurately calculate the exact molar concentration of O$_2^{-\bullet}$ in these reactions. However, (1) is extremely capable of scavenging the hydroxyl free radical (OH$^\bullet$) with 0.22 mM required to reduce this free radical (0.18 mM OH$^\bullet$—chemically generated) by 50%. This is an important biological and chemical property of (1) since OH$^\bullet$ is believed to be more detrimental to cell death directly than O$_2^{-\bullet}$. On the other hand, (1) has no effect in reducing the lipid free radical LOO$^{-\bullet}$.

Isopestacin (1) is antimycotic, with total inhibition of *Pythium ultimum*, a plant pathogenic oomycete, at 40 µg/ml at 48 hr. However, (1) has no inhibitory effect on some other plant pathogenic fungi—*Sclerotinia sclerotiorum* and *Rhizoctonia solani*.

Example 2

Isolation of Pestacin

The *Pestalotiopsis microspora* 12-30 strain was isolated as outlined above. The fungus was grown on the M1D medium and then the culture fluid extracted with 2 equal volumes of methylene chloride. Biological activity against *Pythium ultimum* was used to guide purification of a product that was crystallized after purification by silica gel column chromatography. The product was shown to be homogeneous by thin layer chromatography in a number of solvent systems. The yield of this product was about 20 mg per liter of culture medium. After structural elucidation by x-ray crystallography, the compound was shown to be an 1,3-dihydro isoberzofuran and was termed pestacin (FIG. 3).

The structure of pestacin was established by X-ray diffraction of a crystal grown from a CH$_2$Cl$_2$ solution. Pestacin crystallizes in the P-1 space group and contains one molecule per asymmetric unit (FIG. 5). Three other naturally occurring 1,3-dihydro isobenzofurans have been previously observed. However, pestacin represents the first 1,5,7 trisubstituted natural product. Crystallographic data have been deposited with the Cambridge Crystallographic Data Centre as supplementary publication numbers CCDC 194690. Other crystallographic information is included in the experimental section.

Reference NMR $^{13}$C and $^1$H data were collected using the 2D INADEQUATE and HMQC techniques, respectively. All NMR data are consistent with the X-ray structure. Especially relevant is the observation of the shifts at carbons 1 and 3 at 79.8 and 74.5 ppm, respectively, supporting the assignment of the heteroatom as oxygen. Since other structural data are known from X-ray analysis, these two NMR experiments alone are sufficient to unambiguously establish all shifts. NMR parameters used are included in the experimental section.

Pestacin occurs naturally as a racemic mixture of 1S and 1R enantiomers as indicated by its crystallization into a centrosymmetric space group. This racemization likely occurs post-biosynthetically as enzyme mediated reactions occur with stereospecificity. A racemization mechanism that proceeds through a cationic intermediate is thus proposed here (FIG. 6). This intermediate has the desirable feature of being stabilized by seven resonance structures. These intermediates are further stabilized by their ability to tautomerize into the three neutral ortho-quinone methide-like structures shown in FIGS. 7 (1a–1c). A similar cationic intermediate has been previously demonstrated to occur in synthetic 1-phenyl 1,3-dihydro isobenzofuran, (Wolfgang, K.; Kund, K. *J. Org. Chem.* 1990, 55, 2325–2332) lending support to the mechanism proposed in this natural product. The racemization of 1-aryl substituted 1,3-dihydro isobenzofurans may also occur generally as suggested by the complete absence of stereochemical data for 1-aryl substituted synthetic products despite numerous studies. (Azzena, U.; Demartis, S.; Fiori, 1. G.; Melloni, G.; Pisano, L. *Tetrahedron Lett.* 1995, 36, 8123–8126; Azzena, U.; Demartis, S.; Melloni, G. *J. Org. Chem.* 1996, 61, 4913–4919; Neidlein, R.; Krämer, B. *Chem. Ber.* 1991, 124, 353–356; Bradsher, C. K.; Hunt, D. A. *J. Org. Chem.* 1980, 45, 4248–4250; Kirmse, W.; Kund, K. *J. Am. Chem. Soc.* 1989, 111, 1465–1473 Matsui, K. *Nippon Kagaku Zasshi* 1961, 82, 1382–1385; Delacroix, T.; Bérillon, L.; Cahiez, G.; Knochel, P. *J. Org. Chem.* 2000, 65, 8108–8110.) In addition, isopestacin occurs naturally as a racemic mix, supporting the generality of this racemization.

The similarity of pestacin to isopestacin, described herein and in Strobel, G. A.; Ford, E.; Worapong, J.; Harper, J. K.; Arif, A. M.; Grant, D. M.; Fung, P.; Chau, R. M. W. *Phytochem.* 2002, 60, 179–183, hereby incorporated by reference in its entirety, suggests that pestacin may also exhibit such activity. Pestacin was thus analyzed using the total oxyradical scavenging capacity (TOSC) assay. This analysis assesses a compounds ability to inhibit a free radical initiator's oxidation of α-Keto-γ-methiolbutyric acid to release ethylene gas. Compounds with antioxidant properties thus decrease the production of ethylene gas, as measured gas chromatographically. Pestacin required a 1.7±0.1 mM solution to reduce the effects of the free radical initiator by 50%. In contrast, the water-soluble vitamin E derivative, troxol, required an 18.8±0.9 mM solution to exert the same effect. Pestacin, therefor, appears to be an extremely effective antioxidant as measured by this assay. A mechanism for antioxidant activity may also be proposed based on the structure of pestacin.

Antioxidant activity of pestacin is postulated to involve reaction with reactive oxygen species to afford an oxygen radical species (2) which is converted to a stabilized, doubly benzylic radical, (3), after a five-centered radical abstraction (Figure). There is considerable literature precedent correlating the stability of derived oxygen radicals and anti-inflammatory/antioxidant activity of phenols (Zhang, H.-Y.; Sun, Y.-M.; Wang, X.-L. *J. Org. Chem.* 2002, 67, 2709–2712; Ruiz, J.; Perez, A.; Pouplana, R. *Quant Struct.-Act Relat.* 1996, 15, 219–223) This chain breaking antioxidant mechanism of (1) is likely similar to other natural phenolics such as curcumin, (Sun, Y. M.; Zhang, H.-Y.; Chen, D.-Z.; Liu, C.-B. *Org. Lett.* 2002, 4, 2909–2911) tea catechins and flavanoids, (Sang, S.; Cheng, X.; Stark, R. E.; Rosen, R. T.; Yang, C. S.; Ho, C.-T. *Bioorg. Med. Chem.* 2002, 10, 2233–2237) and the polyisoprenylated benzophenone, garcinol (Sang, S.; Pan, M.-H.; Chang, X.; Bai, N.; Stark, R. E.; Rosen, R. T.; Lin-Shiau, S.-Y.; Lin, J.-K.; Ho, C.-T. *Tetrahedron* 2001, 57, 9931–9938). Future experiments involving reaction of (1) with stable radicals such as 2,2-diphenyl-1-picrylhydrazyl (DPPH) should shed further light on the specific antioxidant mechanism of (1).

Pestacin was also analyzed for antifungal activity using previously described methodology. Inhibition of *Pythium ultimum*, an important root invading pathogen, was observed with a minimum inhibitory concentration of approximately 10 μg per mL. This level of activity is slightly greater than that previously observed for isopestacin.

Experimental.

P. Microspora and Pestacin Isolation

*Pestalotiopsis microspora* (isolate 12-30) was grown for 3 weeks in still culture at 23° C. on the M1D medium. The medium, free of the fungal mycelium, was extracted twice with equal volumes of methylene chloride and taken to dryness by rotary evaporation. The residue was dissolved in a minimal amount of chloroform and passed through a column of silica gel (2.5 cm, 40 μm particle diameter). Chloroform was then passed over the column and (1) eluted in the 100 ml fraction (±20 mL). Elution of (1) was determined by silica gel TLC and fractions containing partially purified (1) combined. Further purification was achieved on the column described above using chloroform/acetonitrile (100/1 v/v) with elution of (1) occurring at 60–75 mL. This later process was repeated until pure (1) was obtained.

Thin Layer Chromatography

Thin layer chromatography of (1) was performed on 0.25 mm Merck silica gel plates with the following $R_f$ values for each system; chloroform/methanol (9/1 v/v), 0.59; chloroform/acetonitrile (6/3 v/v), 0.78; chloroform/ethyl acetate (9/1 v/v), 0.32. Visualization of (1) on TLC plates was achieved under shortwave UV and also by spraying with a 1% solution of vanillin in sulfuric acid followed by gentle heating to form a reddish spot. Cardellina, J. H. *J. Liq. Chromatogr.* 1991, 14, 659–665.

Crystals of (1) were obtained from slow evaporation of a methylene chloride solution at 23° C. The yield of (1) ranged from 16–20 mg per liter of culture fluid.

Pestacin has a molecular weight of 258.089209, as determined by high-resolution mass spectroscopy, consistent with a molecular formula of $C_{15}H_{14}O_4$. An uncorrected melting point of 179–182° C. was measured and UV absorption peaks were observed at 232 and 275 nm (in methanol), with molar extinction coefficients of 3,480 and 3,132, respectively.

X-Ray Crystallographic Methods

X-ray analysis of (1) was performed using a colorless thin plate (0.30×0.23×0.03 mm) mounted on a glass fiber with traces of viscous oil. A Nonius Kappa CCD diffractometer using Mo Kα radiation (λ=0.71073 Å) collected ten frames of data at 200±1 K with an oscillation range of 1°/frame and an exposure time of 20 sec/frame. (COLLECT data collection software. Nonius, B. V. 1998.) Indexing and unit cell refinement based on all observed reflections from those ten frames, indicated a triclinic P lattice. A total of 3990 reflections ($\theta_{max}$=27.5°) were indexed, integrated and corrected for Lorentz polarization and absorption effects using DENZO-SMN and SCALEPAC. (Otwinowski, Z.; Minor, W. *Methods Enzymol.* 1997, 276, 307–326) Post refinement of the unit cell gave a=4.5431(5) Å, b=10.4265(10) Å, c=13.5157(16) Å, α=71.102(5), β=84.634(5), γ=87.145(7) and V=602.93(11) Å³. Axial photographs and systematic absences were consistent with the compound having crystallized in the triclinic space group P-1. Structure was solved by a combination of direct and heavy atom methods using SIR 97. (Altomare, A.; Burla, M. C.; Camalli, M.; Cascarano, G.; Giacovazzo, C.; Guagliardi, A.; Moliteni, G.; Polidori, G.; Spagna, R. 1997, SIR97 (Release 1.02). All of the non-hydrogen atoms were refined with anisotropic displacement coefficients. Hydrogen atoms were located and refined isotropically using SHELXL97. (Sheldrick, G. M. 1997, SHELX97 (including SHELXS97, SHELXL97, CIFTAB). Programs for Crystal Structure Analysis (Release 97-2). University of Göttingen, Germany).

NMR Analyses

Carbon and ¹H NMR shift assignments were established using the INADEQUATE and HMQC experiments, respectively and are consistent with the X-ray structural determination of (1). The 2D INADEQUATE experiment was performed on 73 mg of (1) dissolved in 0.2 ml of CD₃OD and placed in a Shigimi tube designed to center the sample within the coil with glass plugs susceptibility matched to the solvent extending beyond the coil. Analysis was performed on a Varian INOVA 500 MHz spectrometer operating at 125.76 MHz. Spectral widths of 20.0 kHz were used in both dimensions with digital resolutions of 156.3 and 0.2 Hz/point acquired in the evolution and acquisition dimensions, respectively. Other parameters included a $^{13}$C 90° pulse width of 4.8 μs, a temperature of 26° C., a $^1J_{CC}$ value of 65 Hz, and 128 evolution increments of 256 scans each collected. The spectrum was referenced to the central line of CD₃OD at 49.15 ppm. All $^{13}$C assignments were established using a computer program designed to enhance signal detection. (Dunkel, R., Mayne, C. L.; Curtis, J.; Pugmire, R. J.; Grant, D. M. *J. Magn. Reson.* 1990, 90, 290–302; Dunkel, R.; Mayne, C. L.; Pugmire, R. J.; Grant, D. M. *Anal. Chem.* 1992, 62, 3133–3149).

Antioxidant Activity

Antioxidant activity of (1) was assessed by dissolving 8.7 mg of (1) in 200 μL of DMSO then diluting the solution 1:10, 1:100, and 1:1000 in DMSO. A 10 μL volume of each sample was then combined in a 10 mL vial with 100 μL of 100 mM potassium phosphate buffer, 100 μL of 2 mM α-keto-γ-methiolbuthric acid (KMBA), and 690 μL of H₂O. Control samples were also prepared containing 100 μL of 100 mM potassium phosphate buffer, 100 μL of 2 mM KMBA, and 700 μL of H₂O. The sealed samples were then incubated at 37° C. for 5 minutes followed by injection of 100 μL of the free radical initiator, 2,2'-azobis(2-methylpropionamidine) (ABAP). Peroxy radicals, generated by thermal homolysis of ABAP at 37° C., then oxidized KMBA to produce ethylene gas. Ethylene production was monitored by gas chromatography of 1 mL samples removed every 12 minutes over a 96-minute period. Chromatographic analysis was performed on a Hewlett-Packard 5890A gas chromatograph equipped with a Supelco 6-foot Porpak Q packed column, a flame ionization detector, and employing helium as a carrier gas (30 mL/min). The inlet, oven and detector temperatures used were 160°, 60° and 220° C., respectively. Data an lysis was performed on a Hewlett-Packard Chemstation using integrated peak area. All analyses were repeated four times and results averaged.

What is claimed is:

1. A biologically pure compound having the formula:

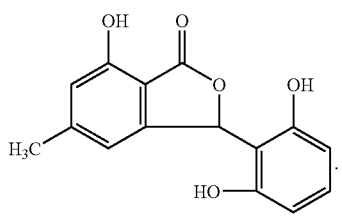

2. A biologically pure compound having the formula:

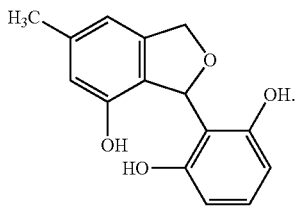

3. A pharmaceutical composition comprising the compound according to claim 1 and a pharmaceutically acceptable carrier.

4. A pharmaceutical composition comprising the compound according to claim 2 and a pharmaceutically acceptable carrier.

5. A method of producing isopestacin comprising:
   a. growing the culture in culture medium under conditions wherein the compound according to claim 1 is made; and
   b. isolating the compound from culture medium.

6. A method of producing pestacin comprising:
   a. growing the culture in culture medium under conditions wherein the compound according to claim 2 is made; and
   b. isolating the compound from culture medium.

7. A method of reducing free radicals in an organism comprising administering the compound of claim 1 or 2 to said organism.

8. A method according to claim 7 wherein said organism is a human.

9. A method of inhibiting the proliferation of a fungus comprising contacting said fungus with a compound according to claim 1 or 2.

* * * * *

UNITED STATES PATENT AND TRADEMARK OFFICE
CERTIFICATE OF CORRECTION

PATENT NO. : 7,192,939 B2
APPLICATION NO. : 10/356320
DATED : March 20, 2007
INVENTOR(S) : Strobel et al.

It is certified that error appears in the above-identified patent and that said Letters Patent is hereby corrected as shown below:

In the Specification:
In column 6, lines 66-67, "moieties herein" should be --moieties" herein--.
In column 9, line 65, "need" should be --noted--.
In column 13, line 35, "utilize" should be --utilized--.
In column 14, line 5, "halide olefin" should be --halide, olefin--.
In column 16, line 30, "Antioxidant" should be --"Antioxidant--.
In column 16, line 6, "sold" should be --solid--.
In column 17, line 35, "must "acceptable" " should be --must be "acceptable"--.
In column 19, line 20, "fixed" should be --mixed--.
In column 19, line 27, "agent" should be --agents--.
In column 19, line 56, "coating" should be --coatings--.
In column 19, line 57, "may a so be" should be --may also be--.
In column 19, line 60, "proportion" should be --proportions--.
In column 19, line 64, "composition" should be --compositions--.
In column 20, line 6, "micron-capsulated" should be --micro-encapsulated--.
In column 21, line 12, "solutions dispersions" should be --solutions or dispersions--.
In column 23, line 47, "because its" should be --because of its--.
In column 24, line 13, "V/v" should be --v/v--.
In column 24, line 14, "ethyl acetate: 9:1" should be --ethyl acetate 9:1--.
In column 24, line 32, "or Lorentz" should be --for Lorentz--.
In column 24, line 50, "$\|Fo|=|Fc\|$" should be --$\|Fo|-|Fc\|$--.
In column 25, line 12, "1992" should be --1992).--.
In column 25, lines 33-34, "frequency 9.787" should be --frequency of 9.787--.
In column 25, line 54, "used trap" should be --used to trap--.
In column 26, line 47, "fit lid" should be --fluid--.
In column 26, line 53, "number solvent" should be --number of solvent--.
In column 27, line 6, "ether" should be --either--.
In column 27, line 9, "benzene rig" should be --benzene ring--.
In column 27, line 35, "no" should be --not--.
In column 28, line 37, "Fiori, 1. G.;" should be --Fiori, M. G.;--
In column 28, line 42, "1465-1473 Matsui" should be --1465-1473; Matsui--.
In column 30, line 4, "$\theta_{max=}27.5°$" should be --$\theta_{max}=27.5°$--.
In column 30, 56, "Peroxy radicals" should be --Peroxyl radicals--.

UNITED STATES PATENT AND TRADEMARK OFFICE
CERTIFICATE OF CORRECTION

PATENT NO. : 7,192,939 B2
APPLICATION NO. : 10/356320
DATED : March 20, 2007
INVENTOR(S) : Strobel et al.

It is certified that error appears in the above-identified patent and that said Letters Patent is hereby corrected as shown below:

In column 30, line 65, "an lysis" should be --analysis--.

Signed and Sealed this

Tenth Day of July, 2007

JON W. DUDAS
*Director of the United States Patent and Trademark Office*

SEQUENCE LISTING

<160> NUMBER OF SEQ ID NOS: 1

<210> SEQ ID NO 1
<211> LENGTH: 466
<212> TYPE: DNA
<213> ORGANISM: Pestalotiopsis sp. NG12-30
<300> PUBLICATION INFORMATION:
<308> DATABASE ACCESSION NUMBER: GenBank Acc. No. AF377301
<309> DATABASE ENTRY DATE: 2002-06-02
<313> RELEVANT RESIDUES: (1)..(466)

<400> SEQUENCE: 1

```
tagagttttc taaactccca acccatgtga acttaccttt tgttgcctcg gcaggagtta      60
taggtcttct tatagctgct gccggtggac cattaaactc ttgttatttt atgtaatctg     120
agcgtcttat tttaataagt caaaactttc aacaacggat ctcttggttc tggcatcgat     180
gaagaacgca gcgaaatgcg ataagtaatg tgaattgcag aattcagtga atcatcgaat     240
ctttgaacgc acattgcgcc cattagtatt ctagtgggca tgcctgttcg agcgtcattt     300
caacccttaa gcctagctta gtgttgggaa tctacttctt tatagttgta gttcctgaaa     360
tacaacggcg gatttgtagt atcctctgag cgtagtaatt tttttctcgc ttttgttagg     420
tgctataact cccagccgct aaaccccccaa tttttgtgg ttgacc                     466
```